(12) United States Patent
Ebisawa

(10) Patent No.: US 7,533,989 B2
(45) Date of Patent: May 19, 2009

(54) SIGHT-LINE DETECTION METHOD AND DEVICE, AND THREE-DIMENSIONAL VIEW-POINT MEASUREMENT DEVICE

(75) Inventor: Yoshinobu Ebisawa, Hamamatsu (JP)

(73) Assignee: National University Corporation Shizuoka University (JP)

( * ) Notice: Subject to any disclaimer, the term of this patent is extended or adjusted under 35 U.S.C. 154(b) by 0 days.

(21) Appl. No.: 10/584,635

(22) PCT Filed: Dec. 24, 2004

(86) PCT No.: PCT/JP2004/019311

§ 371 (c)(1),
(2), (4) Date: May 22, 2007

(87) PCT Pub. No.: WO2005/063114

PCT Pub. Date: Jul. 14, 2005

(65) Prior Publication Data

US 2007/0279590 A1  Dec. 6, 2007

(30) Foreign Application Priority Data

Dec. 25, 2003 (JP) ............................. 2003-429344
Jan. 14, 2004 (JP) ............................. 2004-006359

(51) Int. Cl.
*A61B 3/14* (2006.01)
*A61B 3/10* (2006.01)
(52) U.S. Cl. ...................................... 351/208; 351/221
(58) Field of Classification Search .......... 351/200–245
See application file for complete search history.

(56) References Cited

U.S. PATENT DOCUMENTS 6,050,896 A * 4/2000 Hanado et al. ................ 463/32

(Continued)

FOREIGN PATENT DOCUMENTS

JP  7-79914  3/1995

(Continued)

OTHER PUBLICATIONS

International Search Report issued Apr. 19, 2005.

*Primary Examiner*—Mohammed Hasan
(74) *Attorney, Agent, or Firm*—Ostrolenk, Faber, Gerb & Soffen, LLP

(57) ABSTRACT

Method and device for detecting a line-of-sight of a subject and a three-dimensional view-point measurement device. The method uses a first camera, that measures the position of a pupil relative to a coordinate system, a second camera having a light source arranged at a known position in the coordinate system, and forming a corneal reflection center to obtain data of a size of vector r from the corneal reflection center to the pupil center and an angle φ of the vector r relative to a coordinate axis of the coordinate system, and a calculation means for calculating a line-of-sight direction based on information from each camera. In determining a relational formula, a subject is made to gaze at a known point to perform measurement and a relational formula is determined. In a line-of-sight determining stage, the subject is measured again using the relational formula. A three-dimensional view-point measurement device can be configured so as to simultaneously measure the lines-of-sights of both eyes with two cameras and two light sources.

13 Claims, 26 Drawing Sheets

U.S. PATENT DOCUMENTS

| | | | |
|---|---|---|---|
| 6,115,028 A * | 9/2000 | Balakrishnan et al. | 345/157 |
| 6,578,962 B1 | 6/2003 | Amir et al. | 351/209 |

FOREIGN PATENT DOCUMENTS

| | | |
|---|---|---|
| JP | 7-82539 | 9/1995 |
| JP | 2739331 | 1/1998 |
| JP | 10-66678 | 3/1998 |
| JP | 11-56782 | 3/1999 |
| JP | 2988235 | 10/1999 |
| JP | 2002-102172 | 4/2002 |
| JP | 3324295 | 7/2002 |

* cited by examiner

Fig.1
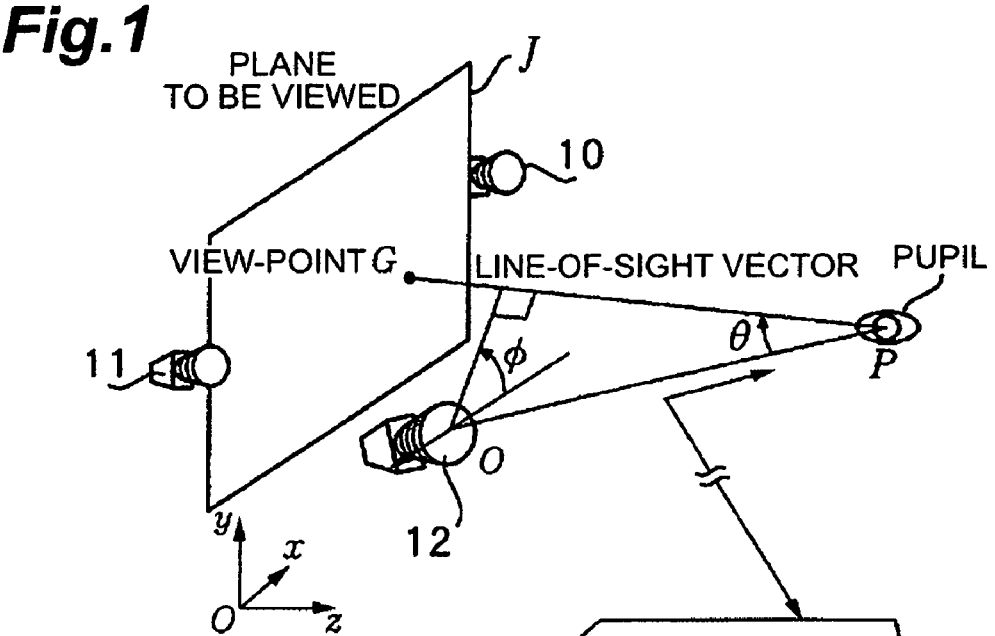
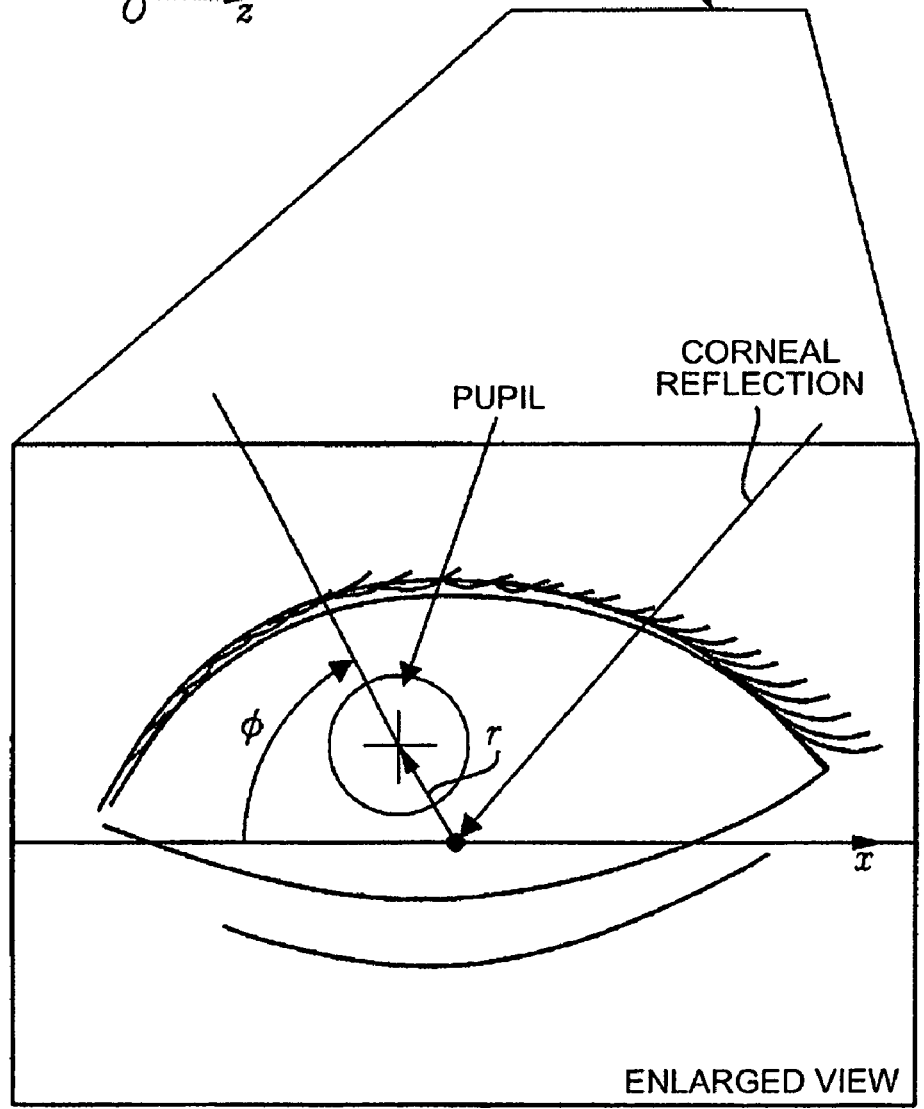

Fig.7
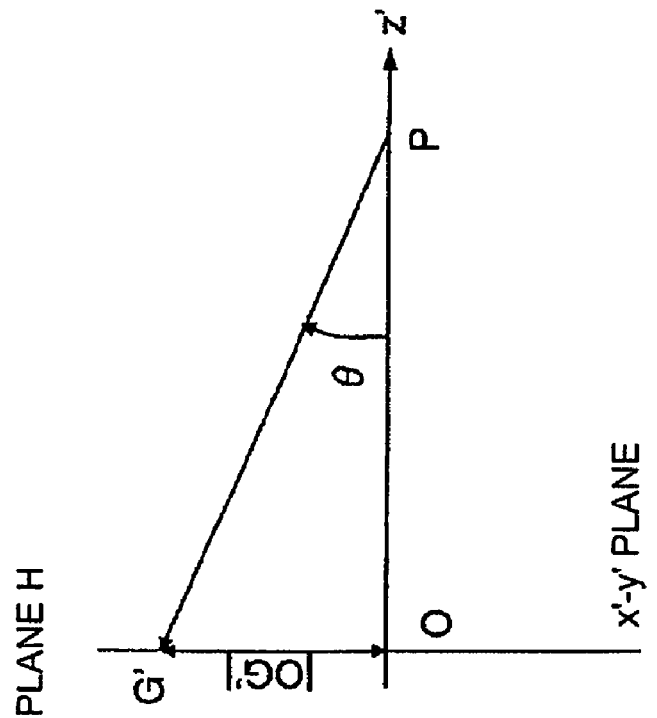
PLANE H
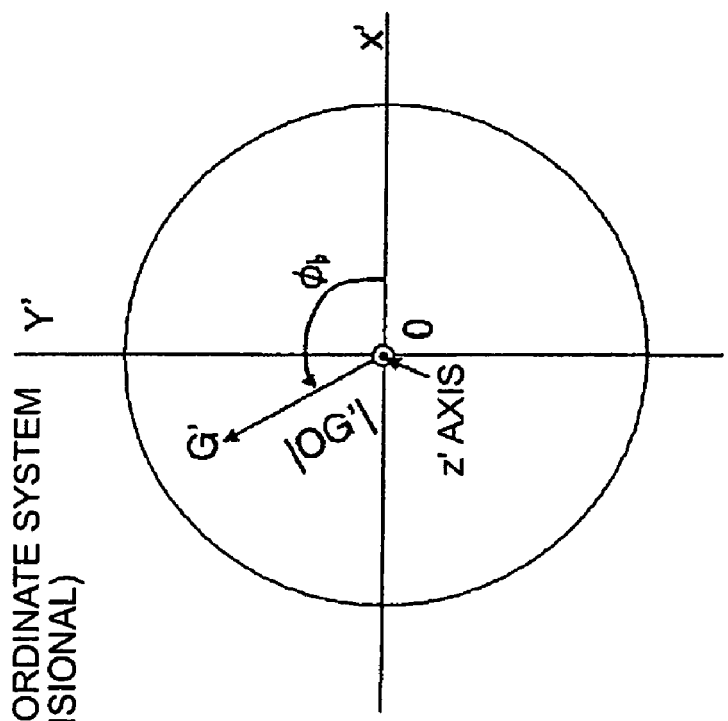
PLANE H COORDINATE SYSTEM
(TWO-DIMENSIONAL)

Fig. 10

| FIELD | LIGHT SOURCE 105 | LIGHT SOURCE 106 | PUPIL TAKEN BY FIRST CAMERA 101 | PUPIL TAKEN BY SECOND CAMERA 102 |
|---|---|---|---|---|
| ODD | ON | OFF | BRIGHT PUPIL | DARK PUPIL |
| EVEN | OFF | ON | DARK PUPIL | BRIGHT PUPIL |
| ODD | ON | OFF | BRIGHT PUPIL | DARK PUPIL |
| EVEN | OFF | ON | DARK PUPIL | BRIGHT PUPIL |
| ODD | ON | OFF | BRIGHT PUPIL | DARK PUPIL |
| EVEN | OFF | ON | DARK PUPIL | BRIGHT PUPIL |
| ODD | ON | OFF | BRIGHT PUPIL | DARK PUPIL |
| EVEN | OFF | ON | DARK PUPIL | BRIGHT PUPIL |

SIGHT-LINE DETECTION METHOD AND DEVICE, AND THREE-DIMENSIONAL VIEW-POINT MEASUREMENT DEVICE

CROSS-REFERENCE TO RELATED APPLICATION

The present application is a 35 U.S.C. §371 national phase conversion of PCT/JP2004/019311 filed Dec. 24, 2004, which claims priority of Japanese application no. JP2003-429344 filed Dec. 25, 2003 and Japanese application no. JP2004-006359 filed Jan. 14, 2004 which are incorporated herein in their entirety.

1. Technical Field

A line-of-sight detection method and device according to the present invention relate to a line-of-sight detection method and line-of-sight detection device that can minimize postural limitations of a subject and detect a line-of-sight without attaching markers, and a three-dimensional view-point measurement device relates to a device that measures a three-dimensional view-point by simultaneously detecting line-of-sight directions of human both eyes.

2. Background Art

Since line-of-sight detection methods and line-of-sight detection devices have been expected to be used for a wide range of application such as medical inspection and man-machine interfaces (line-of-sight input), many proposals have been made. Most of them use a basic principle of detecting a line-of-sight by using a corneal reflection point and a pupil center. The invention described in Patent Document 2 is one relating to the aforementioned detection and is directed to detecting feature points. The invention described in Patent Document 3 makes an in-depth proposal for measurement that takes a shape of cornea into account.

In addition, many line-of-sight detection devices that have been proposed can roughly be divided into a type that mainly fixes a head of a subject and another type that mounts a detection device on the head of the subject. Both types of devices have hindered everyday behavior of the subject seriously and put an enormous load on the subject when performing line-of-sight measurement. Further, recently, non-contact type has been designed for the purpose of reducing the load on the subject, but such type of detection devices is only placed remotely from the subject and has a very limited measuring range, virtually immobilizing the subject for measurement. A method for detecting a line-of-sight from an image of eyes using image processing etc., which has been proposed as a method for eliminating restrictions on movement of the subject, has poor time characteristics requiring a long time for image processing.

Conventional detection devices also have shortcomings of low precision because the same camera used for face detection is also used for line-of-sight detection. To solve this problem, a non-contact line-of-sight measurement device described in Patent Document 1 requires a spectacle frame with three markers attached on a face. If the spectacles are attached, general glasses for vision correction cannot be put on. Also for a user or subject who usually does not wear glasses, the spectacles for measurement become a burden.

Background technology for the three-dimensional view-point measurement device will be described below.

In Patent Document 4 (Japanese Patent No. 2739331: ATR), a technology is described that detects a pupil by using retinal reflection, captures a three-dimensional position of a pupil center 30 from face images taken by two cameras, and determines the position by triangulation. This can be considered to be detecting a three-dimensional position of a pupil. Moreover, illumination light of different wavelengths must be prepared.

In the Patent Document 1 (Japanese Patent Application Laid-open No. Hei 10-066678: NTT, NAC), a technology is described that attaches three markers on a face, detects an eyeball position using a stereo camera having two wide cameras, and tracks the eyeball using one narrow camera.

In Patent Document 5 (Japanese Patent No. 2988235: Nissan Motor Co., Ltd.), a technology is described that determines a center of corneal sphere from corneal reflection images with a plurality of illuminations and determines a line-of-sight direction from the center of corneal sphere and a pupil center.

In Patent Document 6 (Japanese Patent No. 3324295: Nissan Motor Co., Ltd.), like the Patent Document 5, a technology is described that determines a center of corneal sphere from corneal reflection images with a plurality of illuminations and determines a line-of-sight direction from the center of corneal sphere and a pupil center. These technologies are all intended strictly for detecting the line-of-sight direction and do not determine the position of a view-point to which the line-of-sight is directed.

Patent Document 1: Japanese Patent Application Laid-open No. Hei 10-66678
Patent Document 2: Japanese Patent Application Laid-open No. Hei 11-56782
Patent Document 3: Japanese Patent Application Laid-open No. 2002-102172
Patent Document 4: Japanese Patent No. 2739331
Patent Document 5: Japanese Patent No. 2988235
Patent Document 6: Japanese Patent No. 3324295

DISCLOSURE OF THE INVENTION

A first object of the present invention is to provide a line-of-sight detection method that can detect a line-of-sight while minimizing postural limitations of a subject and without attaching markers, and a line-of-sight detection device for realizing the line-of-sight detection method.

A second object of the present invention is to provide a three-dimensional view-point measurement device for measuring a three-dimensional view-point by simultaneously detecting line-of-sight directions of both eyes of a person.

To achieve the first object, a line-of-sight detection method of a subject described in claim 1 according to the present invention using:

a first camera for measuring the position of a pupil relative to a coordinate system; a second camera having a light source arranged at a known position in the coordinate system and forming a corneal reflection point to obtain data of a size of vector r from the corneal reflection point to a pupil center and an angle $\phi$ of the vector r relative to a coordinate axis of the coordinate system; and a calculation means for calculating the line-of-sight direction for executing steps below based on information from each of the cameras, comprises the stages of:

determining a relational formula, including the steps of:

obtaining data on a coordinate point O of the position of a pupil of a subject with the first camera by making the subject gaze at a known point G in the coordinate system;

obtaining, in the state of the subject, data of the corneal reflection point, a size of vector r from the reflection point to a pupil center P, and an inclination $\phi$ of the vector r relative to the coordinate axis with the second camera;

calculating an angle θ between a line connecting a reference position of the second camera and the pupil center and a line-of-sight of the subject by the calculation means; and calculating a formula θ=f(r*) showing a relationship between r* related to r and θ based on the measured values and calculated value; and determining a line-of-sight, including the steps of:

obtaining data on a coordinate point O' of the pupil position of the subject with the first camera by making the subject gaze at an unknown point G' in the coordinate system;

obtaining data of the corneal reflection point, a size of vector r' from the reflection point to the pupil center P, and an inclination φ' of the vector r' relative to the coordinate axis with the second camera; and calculating θ'=f(r*') by using the relational formula to obtain the unknown point G' from the inclination φ' and θ'.

In the method described in claim 2 according to the present invention, r* in the method described in claim 1 is r itself or a corrected value of r based on OP, and r*' is r' itself or a corrected value of r' based on OP'.

In the method described in claim 3 according to the present invention, the first camera is a stereo camera arranged by aligning a baseline in a horizontal axis direction of the coordinate system, and a light source of the second camera is constructed so as to provide an optical axis that is substantially aligned with that of the second camera.

In the method described in claim 4 according to the present invention, the θ=f(r*) showing the relationship between r* and θ is given by θ=k×r* (where k is a constant).

In the method described in claim 5 according to the present invention, the pupil is one of the pupils of the subject.

A device described in claim 6 according to the present invention comprises:

a first camera for measuring a position P of a pupil relative to the coordinate system;

a second camera having a light source arranged at a known position in the coordinate system to obtain data of a size of vector r from a corneal reflection point to a pupil center illuminated by the light source and an angle φ of r relative to the coordinate axis; and a calculation means for executing the steps of:

obtaining data on a coordinate point P of the position of a pupil of a subject with the first camera by making the subject gaze at a known point G in the coordinate system;

obtaining, in the state of the subject, data of the corneal reflection point, a size of vector r from the reflection point to a pupil center P, and an inclination φ of the vector r relative to the coordinate axis with the second camera;

calculating an angle θ between a line connecting a reference position of the second camera and the pupil center and the line-of-sight of the subject and calculating a formula θ=f(r*) showing a relationship between r* related to r and θ;

obtaining data on a coordinate point O' of the pupil position of the subject with the first camera by making the subject gaze at an unknown point G' in the coordinate system;

obtaining data of the corneal reflection point, a size of vector r' from the reflection point to the pupil center P, and an inclination φ' of the vector r' relative to the coordinate axis with the second camera; and calculating θ'=f(r*') from r*' related to r' by using the relational formula to further obtain the unknown point G' from φ' and θ'.

To achieve the second object, a three-dimensional view-point measurement device described in claim 7 according to the present invention comprises:

two cameras, a first light source arranged near one of the two cameras, a second light source arranged near another of the two cameras, a control means for controlling ON/OFF of the first light source and the second light source and obtaining an image signal in sync with ON/OFF, and a calculation means for extracting a pupil and corneal reflection from the obtained image signal.

A device described in claim 8 according to the present invention comprises:

two cameras, a first light source arranged near one of the two cameras, a second light source arranged near another of the two cameras, a control means for controlling ON/OFF of the first light source and the second light source and obtaining an image signal in sync with ON/OFF, and a calculation means for extracting a pupil and corneal reflection from the obtained image signal and calculating a line-of-sight vector from these positions.

A device described in claim 9 according to the present invention comprises:

two cameras, a first light source arranged near one of the two cameras, a second light source arranged near another of the two cameras, a control means for controlling ON/OFF of the first light source and the second light source and obtaining an image signal in sync with ON/OFF, and a calculation means for extracting a pupil and corneal reflection from the obtained image signal and calculating a three-dimensional position of the pupil from these positions.

The device described in claim 10 according to the present invention is any of the devices described in claims 7 to 9, wherein:

the first light source and the second light source are configured to have an approximately identical emission wavelength.

As has been described in detail, a line-of-sight detection method of the present invention is a line-of-sight detection method of a subject that uses a first camera for measuring the position of a pupil relative to the coordinate system, a second camera having a light source arranged at a known position in the coordinate system and forming a corneal reflection point to obtain data of a size of vector r from the corneal reflection point to the pupil center and an angle φ of the vector r relative to the coordinate axis, and a calculation means for calculating a line-of-sight direction and for executing the steps below based on information from each of the cameras.

In the stage of determining a relational formula, a formula θ=f(r*) showing a relationship between r* related to r (vector from the corneal reflection point to the pupil center) and θ (angle between the line connecting the second camera and the pupil center and the line-of-sight of the subject) is calculated in advance based on measured values by using the first camera and second camera and a calculated value by the calculation means. Then, in the stage of determining a line-of-sight, θ'=f(r*') is calculated using the aforementioned relational formula and an unknown point G' is obtained from an inclination φ' measured in this stage and θ'.

Therefore, the line-of-sight can be measured without severely constraining a subject.

Since the stage of determining the relational formula is performed for a specific subject and measurement is performed using a relational formula obtained in the stage, there is no room for occurrence of measurement error due to an individual difference of the subject. Consequently, correct data on the line-of-sight can be obtained.

The three-dimensional view-point measurement device of the present invention can measure a three-dimensional view-point by simultaneously detecting the line-of-sight directions of both eyes of a person. Like the aforementioned method, there is no need for severely constraining a person.

BRIEF DESCRIPTION OF THE DRAWINGS

FIG. 1 is a schematic diagram showing an arrangement of embodiments of apparatuses for carrying out a line-of-sight detection method according to the present invention. An enlarged view of an example of a physical relationship between a pupil and a corneal reflection (point) is shown.

FIG. 7 is a diagram for illustrating meanings of θ and φ in the virtual view-point plane (H).

FIG. 10 is a diagram showing a correspondence between turning ON/turning OFF of a light source and a bright/dark pupil.

FIG. 20(a) is the case in which the position of the camera and that of the light source are different. FIG. 20(b) is the case in which the position of the camera and that of the light source are same.

FIG. 21(a) is the case in which the position of the camera and that of the light source are different. FIG. 21(b) is the case in which the position of the camera and that of the light source are same.

EXPLANATION OF NUMERALS

Figure 2:
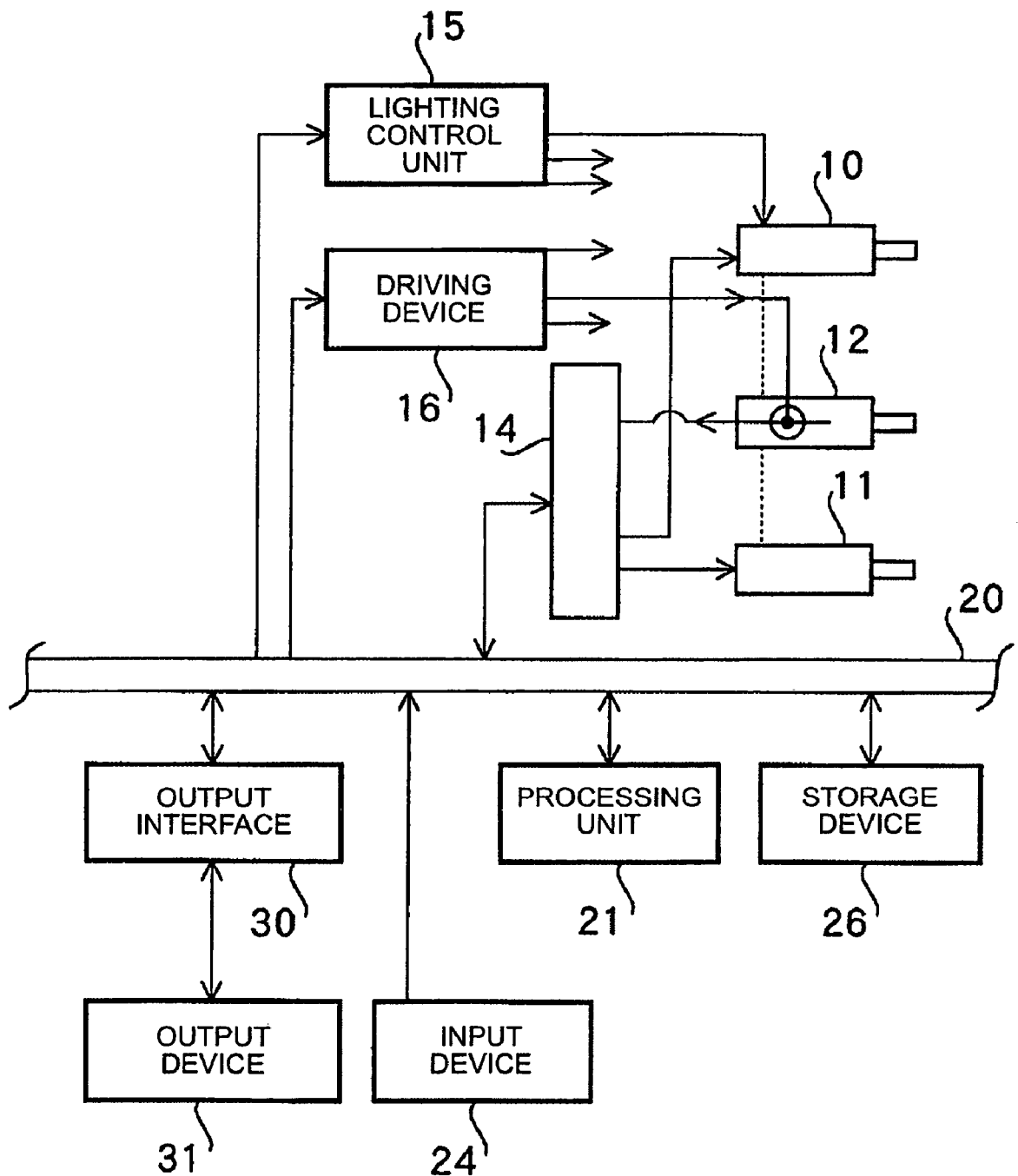
FIG. 2 is a block diagram showing a configuration of apparatuses and the like for carrying out the line-of-sight detection method of the present invention.

10, 11: First camera
12: Second camera
14: Camera interface
15: Lighting control unit
16: Camera driving device
20: Bus line
22: Processing unit (CPU)
24: Input device
26: Storage device
30: Output interface
31: Output device
101, 102: camera
103, 104: Lens
105. 106: Light source
107: Face
108: Pupil
109: Corneal reflection
110: Camera
111: Screen
120: Camera
121: Light source
122: Contact point between a tangent plane of a spherical surface and the spherical surface
123: Center of a spherical surface
124: Spherical surface
125: Tangent plane of a spherical surface
126: Eyeball

BEST MODES FOR CARRYING OUT THE INVENTION

Best modes for carrying out a line-of-sight detection method and device of the present invention will be described in detail below with reference to the drawings.

Figure 4:
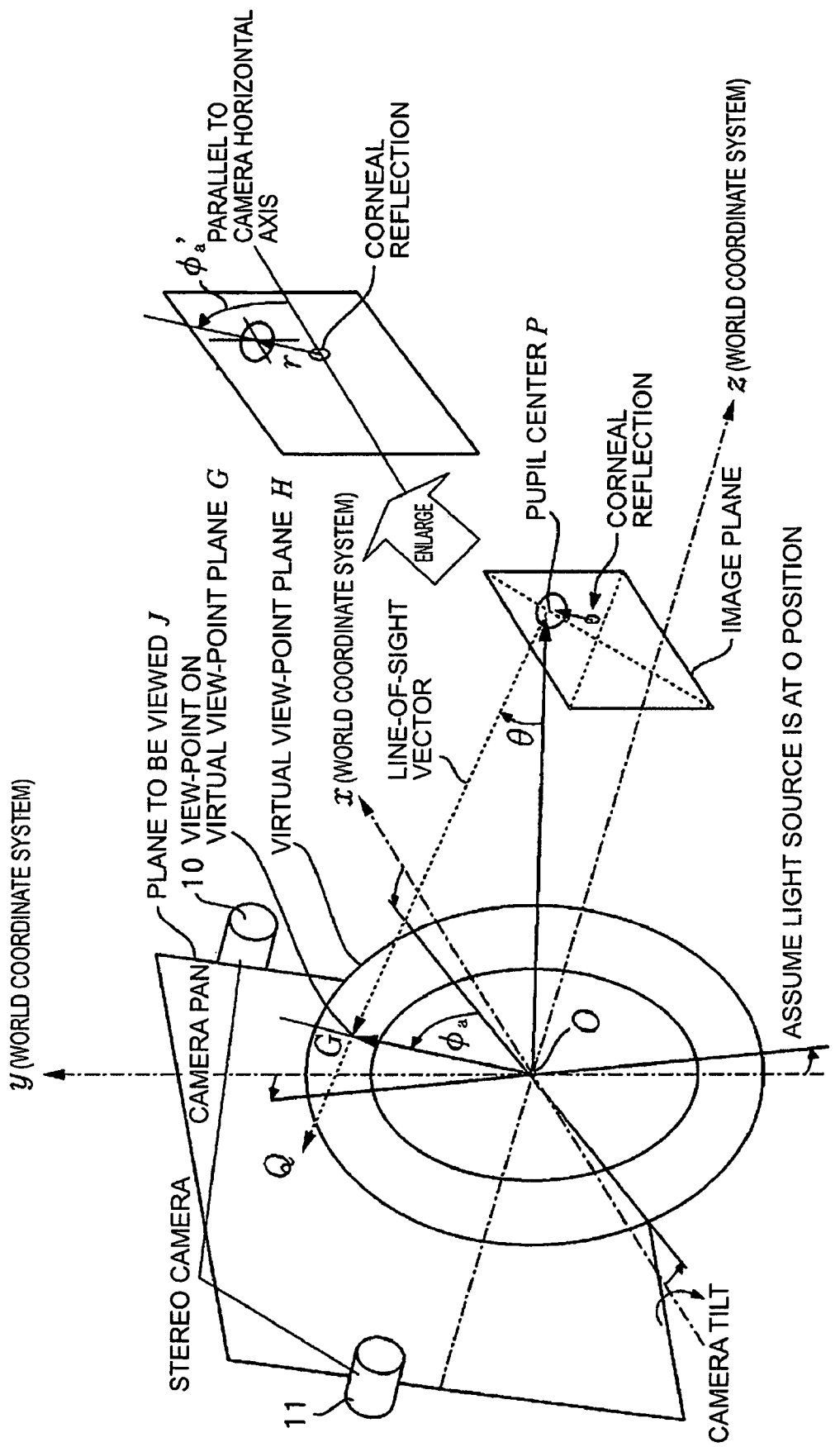
FIG. 4 is a perspective view showing the arrangement of apparatuses in relation to a world coordinate system.

FIG. 1 is a schematic diagram showing an arrangement of an embodiment of apparatuses for carrying out a line-of-sight detection method of the present invention. FIG. 4 is a perspective view showing the arrangement of apparatuses for carrying out the line-of-sight detection method of the present invention in relation to the world coordinate system.

A camera for eyeball shooting with high magnification is used as a second camera 12. This camera is arranged in this embodiment at origin of the world coordinate system, at O (0, 0) in FIG. 4. In FIG. 4, an illustration of the camera 12 is omitted.

FIG. 1 shows an example of the physical relationship of the corneal reflection (point) based on data obtained with the second camera 12 by enlarging it. This image is displayed by an output device described later.

First camera 10, 11 is a stereo camera composed of two cameras and for detecting a three-dimensional position of a pupil.

The distance (base length) between the first cameras 10, 11 is parallel to the X axis of the world coordinate system.

The second camera 12 is sighted at least on one pupil and shown in FIG. 1 by enlarging it. Data of the corneal reflection point and the pupil center is obtained.

An illumination means (not shown) is provided integrally or in connection with the first camera 10, 11 and the second camera 12 respectively.

FIG. 2 is a block diagram showing the configuration of apparatuses for carrying out the line-of-sight detection method of the present invention.

Image output obtained by CCDs of the first camera 10, 11 and the second camera 12 is connected to a bus line 20 via an interface 14.

In this embodiment, the second camera 12 has a light source provided at a known position O in the coordinate system and forming a corneal reflection point to obtain data of the size of vector r from the corneal reflection point to the pupil center and the angle θ of the vector r relative to the coordinate axis. In this embodiment, an optical axis of light from the light source is provided so that the optical axis is aligned with that of the second camera 12.

The second camera 12 is supplied by a signal supplied from a processing unit (CPU) 21 via a driving device 16 and is sighted (directed and focused) on a target eye.

An operator operates an input device 24 for sighting when necessary while viewing an eye image (See FIG. 1) displayed in a display screen forming part of an output device 31. The illumination means (not shown) for each camera is operated by a signal from a lighting control unit 15.

In a storage device 26, programs for executing control described later and a RAM area for performing operations are provided. Image information of a subject, operation result information, system operation information and so on are output to the output device 31 via an output interface 30. The output device 31 includes an image display device, a printer and so on.

The first camera 10, 11 is provided to detect a three-dimensional position on coordinates of the pupil center of eye. The second camera 12 is a camera for detecting a line-of-sight with high magnification and captures only an image of a surrounding eye including a pupil.

An automatic tracking control means (driving device 16) is provided to track one or both of two eyes based on three-dimensional pupil position information from the first camera.

It is also possible to manually align the optical axis of a camera. As will be described later, a line-of-sight vector is determined from the three-dimensional pupil position P obtained from output of the first camera 10, 11, and the position of the center of a corneal reflection image and the pupil center P obtained from output of the second camera 12.

Figure 13:
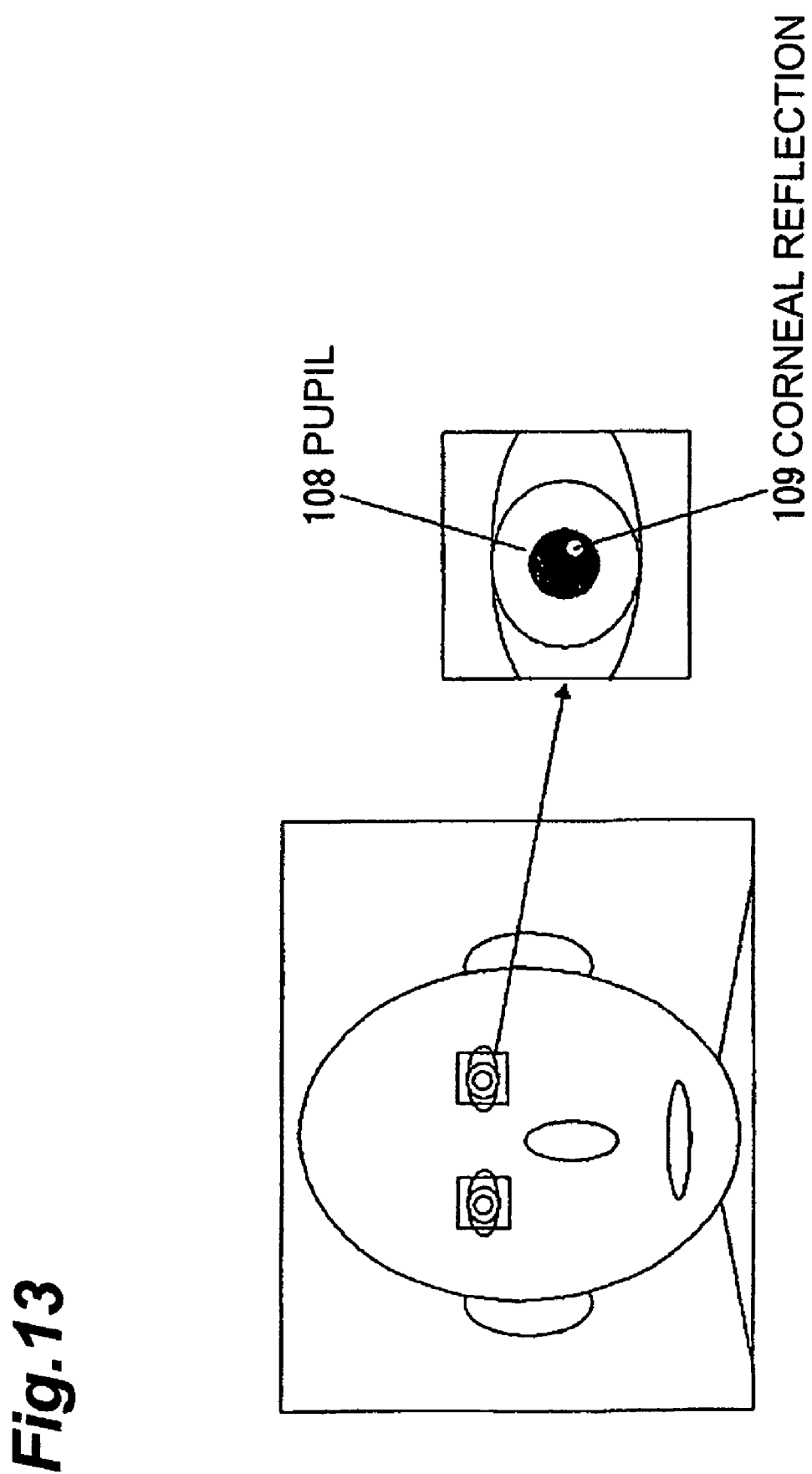
FIG. 13 is a diagram showing a whole face and a range to be tracked.

(About illumination light sources) Illumination light sources to be prepared can include ones arranged in or near an aperture of a camera lens (hereinafter referred to as inside light sources) and ones arranged apart from the aperture (hereinafter referred to as outside light sources). In images of inside light sources, pupils tend to appear brighter than other parts of a face. This is described in connection with FIG. 13B in Japanese Patent No. Hei 7-82539.

Conversely, pupils tend to appear darker than other parts due to outside light sources. This is described in connection with FIG. 13C of the same.

By synchronizing the inside and outside light sources with a video signal to turn on alternately and producing an image difference by taking an obtained latter image from an obtained former image in real time, other parts than the pupils disappear by canceling out each other, making it easier to detect only the pupils. Such a light source is provided for each camera.

In this embodiment, light sources are mounted for total three cameras of the first and second cameras.

In order to prevent light emitted by light sources of other cameras and reflected by the spectacles from being taken in an image as a spectacle reflection image due to this configuration, light sources of different center wavelengths are used as light sources to be mounted on each camera and a band-pass filter with each wavelength as the center wavelength is mounted on each camera.

In this case, when generally an emission wavelength band of light source has a wide band, the emission wavelength overlaps in three or more light sources, and therefore the light sources of each other's camera interfere even if the selected band-pass filter has a narrow band.

To prevent this, a band-pass filter is placed before a light source, the wavelength band of light caused to be emitted to a face is narrowed, overlapping of the emission wavelength band is reduced as much as possible, and further before each camera a band-pass filter is placed which has almost the same center wavelength as that of the band-pass filter placed before the light source of the same camera so that mutual interference can be eliminated.

Figure 3:
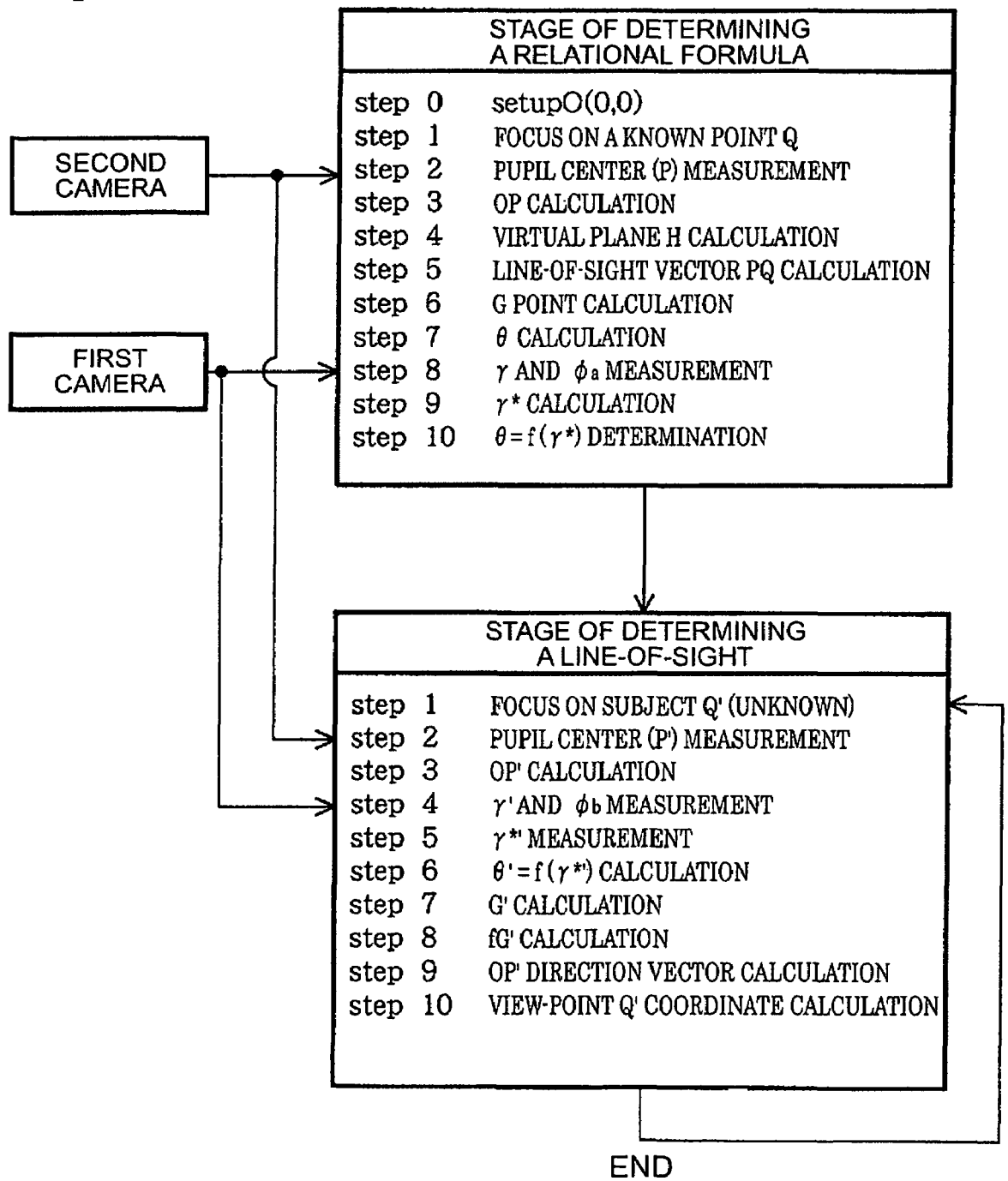
FIG. 3 is a flow chart for describing the line-of-sight detection method according to the present invention.

A line-of-sight detection method of the present invention will be described below with reference to FIGS. 3 and 4. The line-of-sight detection method according to the present invention comprises a stage of determining a relational formula for determining a relational formula and a stage of measuring a line-of-sight for determining any line-of-sight of a subject based on the determined relational formula.

The stage of determining a relational formula includes the steps 0 to 10 and the stage of measuring a line-of-sight includes the steps 1 to 10.

FIG. 4 shows an arrangement of apparatuses and the like and related planes and the like for carrying out the line-of-sight detection method of the present invention in connection with the world coordinate system.

[Stage of Determining a Relational Formula]

(Step 0) Assignment of the position of each camera relative to the world coordinate system.

Define the origin of the world coordinate system as O (0, 0) and arrange the first camera.

(Step 1) Make a subject gaze at a known point.

Make a subject gaze at a point Q $(x_Q, y_Q, z_Q)$ whose coordinates in the world coordinate system are known.

(Step 2) Acquisition of coordinate position data of the pupil center P of the subject with the second camera.

Determine a three-dimensional coordinate P $(x_P, y_P, z_P)$ of the pupil center with a stereo camera.

(Step 3) Calculation of |OP|

Determine a direction vector $(l_x, l_y, l_z) = (x_P - x_O, y_P - y_O, z_P - z_O)$ of a vector OP and its length $|OP| = [(x_P - x_O)^2 + (y_P - y_O)^2 + (z_P - z_O)^2]^{1/2}$ (Step 4) Calculation of a virtual view-point plane H that is perpendicular to |OP| and passes through O The plane H is given by the following formula:

$$(l_x \cdot x + l_y \cdot y + l_z \cdot z) - (l_x \cdot x_O + l_y \cdot y_O + l_z \cdot z_O) = 0 \qquad (1)$$

(Step 5) Calculation of a vector PQ representing a line-of-sight

A direction vector $(s_x, s_y, s_z)$ of PQ representing the line-of-sight is given by $(s_x, s_y, s_z) = (x_Q - x_P, y_Q - y_P, z_Q - z_P)$ and a straight line PQ is given, because the line passes through P $(x_P, y_P, z_P)$, by the following formula:

$$(x - x_P)/s_x = (y - y_P)/s_y = (z - z_P)/s_z \qquad (2)$$

(Step 6) Calculation of a coordinate G ($x_G$, $y_G$, $z_G$) of an intersection of the straight line PQ and the virtual view-point plane H (x, y, z) determined by setting the aforementioned formula (2)=t is given by the following formula (3):

$$x = s_x t + x_P$$

$$y = s_y t + y_P$$

$$z = s_z t + z_P \quad (3)$$

Substituting (3) into the formula of the plane H determines t:

$$t = (l_x^2 + l_y^2 + l_z^2)/(l_x s_x + l_y s_y + l_z s_z) \quad (4)$$

Substituting (4) into (3) yields the intersection G ($x_G$, $y_G$, $z_G$) in the world coordinate system.

(Step 7) Calculation of an angle θ between the vector OP and vector PG Determine an angle θ formed by the direction vector ($l_x$, $l_y$, $l_z$) of the vector OP and the direction vector PG ($S_G$, $S_G$, $S_G$) of the line-of-sight vector.

$$\theta = \cos^{-1}[l_x s_x + l_y s_y + l_z s_z|/(l_x^2 + l_y^2 + l_z^2)^{1/2} \cdot (s_x^2 + s_y^2 + s_z^2)^{1/2}] \geq 0 \quad (5)$$

(Step 8) Measurement of r and $\phi_a$

Obtain the coordinates of corneal reflection center and pupil center with the first camera (first camera 20) and determine the size of vector r from the corneal reflection center to the pupil center and angle θ (relative to the coordinate axis).

Assuming that the coordinates of corneal reflection center and pupil center detected from an image of the camera for line-of-sight detection (second camera 12) are ($g_x$, $g_y$) and ($p_x$, $p_y$) respectively, the distance and angle can be calculated as shown below:

If $|r| \neq 0$, $$\text{let } |r| = [(p_x - g_x)^2 + (p_y - g_y)^2]^{1/2} \quad (6)$$

$$\text{and } \phi_a = \cos^{-1}(p_y - g_y)/|r| \quad (7)$$

If putting $\phi_a'$ ($0 \leq \phi_a' \leq \pi$),

If $p_x < g_x$, $\phi_a = \phi_a'$

If $p_x > g_x$, $\phi_a = -\phi_a'$

When a subject gazes at Q, determine $|r|$ as $|r_Q|$ (in units of pixels).

(Step 9) Determine $|r^*|$ by correcting $|r|$ with OP.

The second camera 12 detects the center of a corneal reflection image and the pupil center image, and from their relative physical relationship estimates an angle θ formed by the vector OP and a line-of-sight PG.

In this case, when images have different zoom ratios even while viewing in the same direction, a relative relation between the center of a corneal reflection image and the pupil center image changes, and thus the zoom ratio of image is an important element.

To solve this problem, first a relation is measured between the distance and zoom ratio in advance to determine a relational formula. Since the three-dimensional position of a pupil is known, the distance is calculated between the camera for line-of-sight detection and a pupil, and then the zoom ratio is calculated using the relational formula to correct the distance between the center of a corneal reflection image and the pupil center image.

(Step 10) Determine a relational formula f between $|r^*|$ and θ by using θ and $|r^*|$.

Let θ and $|r|$ when a subject gazes at O be $\theta_O$ and $|r_O|$ respectively, since $|r^*_O| = 0$ when $|r_O| = 0$, assume a linear relation $$\theta = k|r^*| \quad (8)$$

between a value θ when Q is viewed by the subject and $|r^*|$ and determine a coefficient k.

$$\text{Let } k = \theta_Q/|r^*_Q| \quad (9)$$

$$\text{and } \phi_a = -\phi_a' \quad (10)$$

By determining such the coefficient k (generally a relational formula f between $|r^*|$ and θ), the line-of-sight is calibrated. $|r^*|$ is a function of θ and is independent of $\phi_a$. This is because it is assumed that k is constant in spite of the value of $\phi_a$ or $\phi_a'$.

This will be further described with reference to FIG. 5. When mapping from ($|r^*|$, $\phi_a'$) to ($|\theta|$, $\phi_a$), the origin is mapped to the origin and mapping is simply scaled and right and left are reversed.

The relational formula obtained in the aforementioned stage of determining a relational formula is used [stage of measuring a line-of-sight].

(Step 1) Sighting on a subject by the first camera if required

The view point of the subject is assumed to be an unknown Q' ($x_Q$, $y_Q$, $z_Q$) of the plane to be viewed.

An object of a procedure below is to determine this coordinate.

(Step 2) Measurement of three-dimensional coordinate of the pupil center

Figure 5:
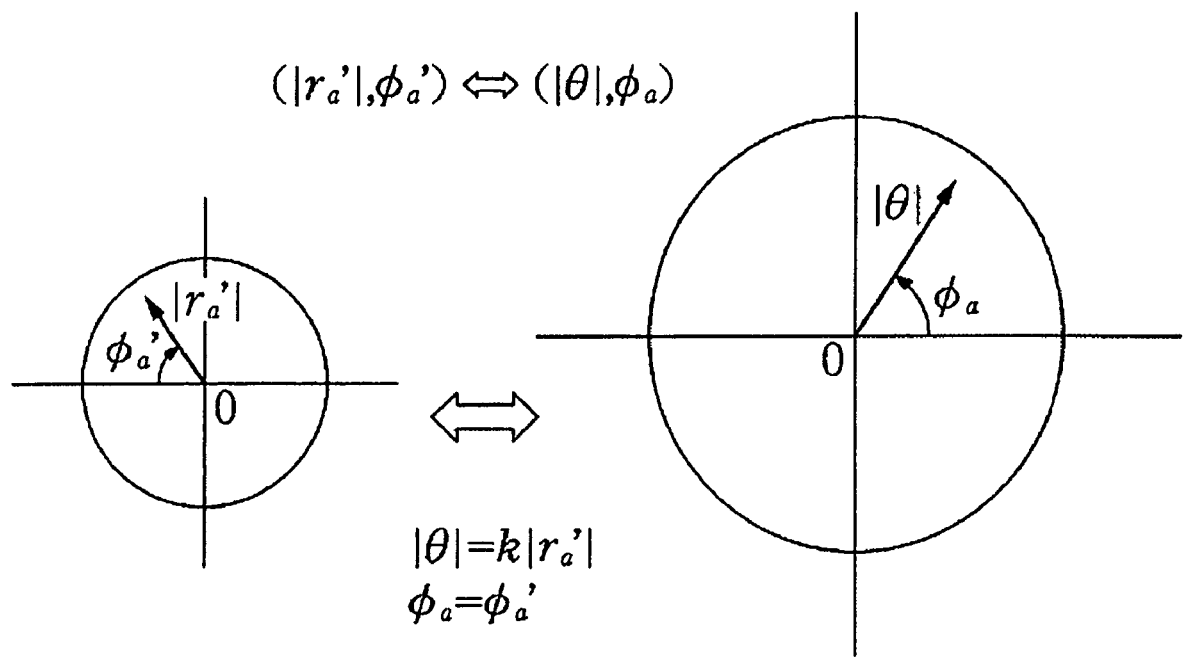
FIG. 5 is a graph illustrating mapping between a pupil and a virtual view-point plane [correspondence between (r', φ) and (|θ|=k|R'|, −φ)].

As shown FIG. 5, measure coordinate position data ($x_P$, $y_P$, $z_P$) of the pupil center P' of a subject using the first camera 10, 12.

(Step 3) Calculation of |OP'|

Determine a direction vector ($l_x$, $l_y$, $l_z$) = ($x_P - x_O$, $y_P - y_O$, $z_P - z_O$) of a vector OP' and its length $|OP'| = [(x_P - x_O)^2 + (y_P - y_O)^2 + (z_P - z_O)^2]^{1/2}$ (Step 4) Measure the size of vector r' and angle $\phi_b$ relative to the coordinate axis by obtaining the coordinates of the center of corneal reflection and the pupil center with the first camera.

If $|r'| \neq 0$, $$\text{let } |r'| = [(p_x - g_x)^2 + (p_y - g_y)^2]^{1/2} \quad (6')$$

$$\text{and } \phi_b = \cos^{-1}(p_y - g_y)/|r| \quad (7')$$

If putting $\phi_a'$ ($0 \leq \phi_b' \leq \pi$),

If $p_x < g_x$, $\phi_b = \phi_b'$

If $p_x < g_x$, $\phi_b = -\phi_b'$ (Step 5) Determine $r^{*'}$ by correcting r' with |OP'|.

(Step 6) Determine θ' using the relational formula determined in the previous stage.

$$\theta' = f(|r^{*'}|) = k|r^{*'}|$$

(Step 7) Determine a line-of-sight vector G'.

Figure 6:
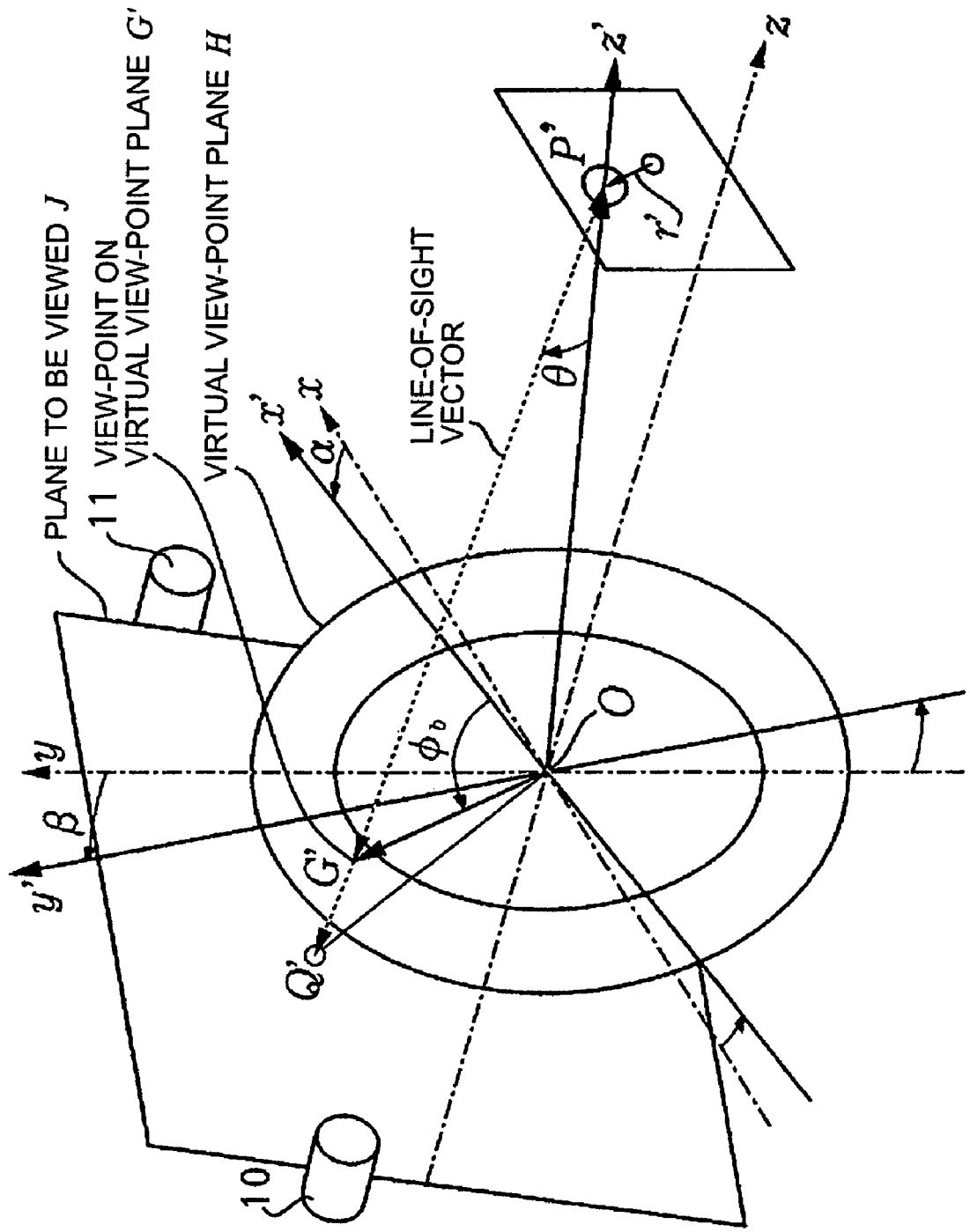
FIG. 6 is a perspective view for illustrating the relationship between a plane to be viewed and a virtual view-point plane (H).

Take an orthogonal coordinate system (with the origin aligned with an absolute coordinate system) by selecting the virtual view-point plane H as an x'–y' plane, as shown in FIG. 6. (The z' axis passes through the point P).

Assume that the x' and y' axes on the plane H are rotated by α in the horizontal direction and by β in the vertical direction relative to the x and y axes in the absolute coordinate system.

FIG. 7 (left) shows a view of the plane H from the z' axis direction and

FIG. 7 (right) shows a plane that passes three points of O, G', and P.

The point G' in the orthogonal coordinate system of the virtual view-point plane H is determined by θ, $\phi_b$, and |OP|.

As is evident from FIG. 7 (right),

|OG'|=|OP|tan θ and $x_G'$, $Y_G'$ of the point G' ($x_G'$, $y_G'$, 0) in the orthogonal coordinate system of the virtual view-point plane H is determined, if $\phi_b=\phi_b'$, by $$x_G'=|OG'|\cos\phi_b'$$

$$y_G'=|OG'|\sin\phi_b'$$

(Step 8) Determine PG'.

Since the coordinate of the point P in the orthogonal coordinate system of the virtual view-point plane H is (|OP|, 0, 0), a line-of-sight vector in the same coordinate system is determined, as a vector PG' connecting from P to G', by $$PG'=(x_G', y_G', -|OP|)$$

This is also a direction vector of the line-of-sight vector in the orthogonal coordinate system of the virtual view-point plane H.

(Step 9) Calculation of a direction vector of the line-of-sight vector The direction vector ($l_x$, $l_y$, $l_z$) of the vector OP in the world coordinate system agrees with the z' coordinate of the orthogonal coordinate system of the virtual view-point plane H. If the x' axis in the orthogonal coordinate system of the virtual view-point plane H is rotated by −α around the origin so that the x' axis agrees with the x axis of the world coordinate system and the y' axis is rotated by −β around the origin so that the y' axis agrees with the y axis, the orthogonal coordinate system of the virtual view-point plane H and the world coordinate system agree. The direction vector of the vector PG' in the orthogonal coordinate system of the virtual view-point plane H after the aforementioned coordinate rotation agrees with the line-of-sight vector in the world coordinate system.

Where Formula (11)

$$\cos\alpha=\frac{l_z}{\sqrt{l_x^2+l_z^2}}, \sin\alpha=\frac{l_x}{\sqrt{l_x^2+l_z^2}}, \cos\beta \qquad (11)$$

$$=\frac{\sqrt{l_x^2+l_z^2}}{\sqrt{l_x^2+l_y^2+l_z^2}}, \sin\beta=\frac{l_y}{\sqrt{l_x^2+l_y^2+l_z^2}}$$

After the rotation, the direction vector ($s_x$, $s_y$, $s_z$) of the line-of-sight vector in the world coordinate system is given by the formula (12) shown below.

Formula (12)

$$\begin{pmatrix}s_z\\s_x\\s_y\end{pmatrix}=\begin{pmatrix}\cos\beta & 0 & -\sin\beta\\0 & 1 & 0\\\sin\beta & 0 & \cos\beta\end{pmatrix}\begin{pmatrix}\cos\alpha & -\sin\alpha & 0\\\sin\alpha & \cos\alpha & 0\\0 & 0 & 1\end{pmatrix}\begin{pmatrix}-|OP|\\x_{G'}\\y_{G'}\end{pmatrix} \qquad (12)$$

Figure 8:
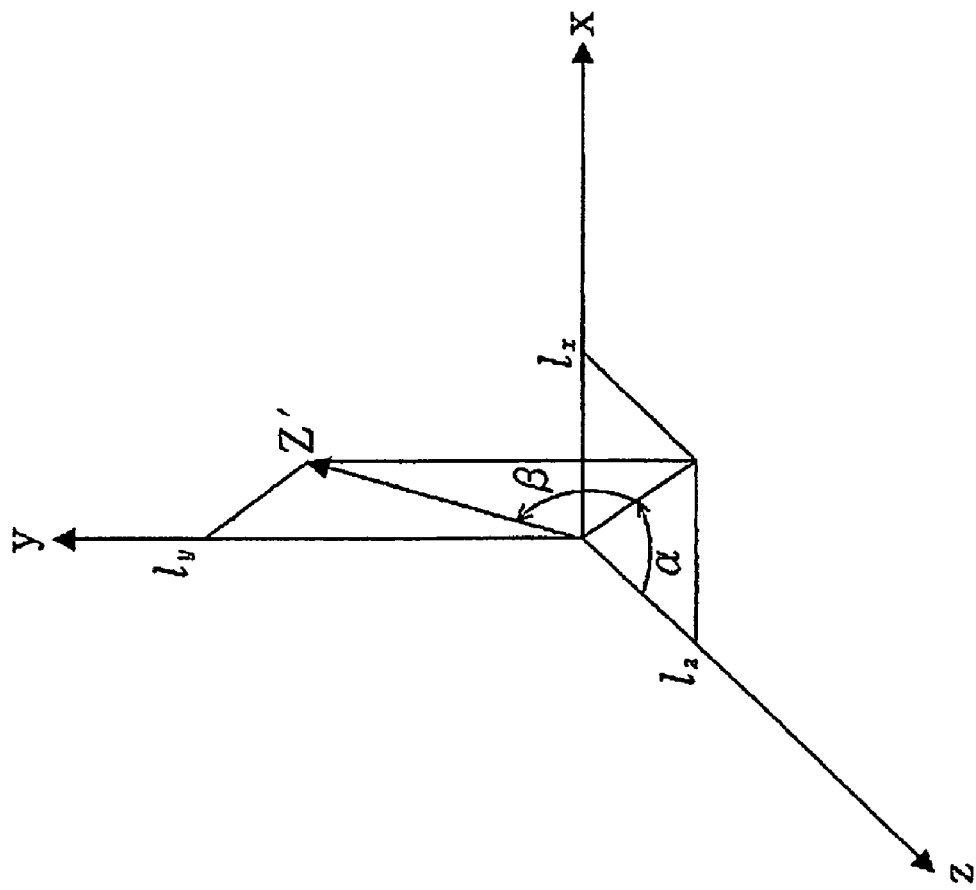
FIG. 8 is a graph showing the relationship between a direction vector and an angle.

Note that FIG. 8 shows relations between the orthogonal coordinate system and angles.

(Step 10) Calculation of a view-point Q'

Using ($s_x$, $s_y$, $s_z$) determined in the previous step, a line-of-sight formula in the world coordinate system is represented by $$(x-x_P)/s_x=(y-y_P)/s_y=(z-z_P)/s_z(=t) \qquad (2)$$

If the visual object is a plane and its formula is given by $$m_x\cdot x+m_y\cdot y+m_z\cdot z+d=0 \qquad (13)$$

an intersection of the formulas (11) and (12) is Q' and it is determined From (2)

$$x=s_x t+x_P$$

$$y=s_y t+y_P$$

$$z=s_z t+z_P \qquad (3)$$

Substituting (3) into the formula of the plane H yields Formula (14)

$$t=\frac{d-(m_x x_P+m_y y_P+m_z z_P)}{m_x s_x+m_y s_y+m_z s_z} \qquad (14)$$

Substituting (14) into (3) determines the view-point Q' ($x_Q'$, $y_Q'$, $z_Q'$).

Different modifications of embodiments of the line-of-sight detection method of the present invention, which has been described in detail, can be expected. These modifications belong to the technical scope of the present invention.

All cameras used can be highly sensitive to near-infrared ray and a fixed-focus lens can be used by stopping down its aperture as much as possible to increase a focus depth.

That is, by creating a state in which a head is always in focus even if the head moves significantly, the camera can have capabilities of always taking the head even if the direction of the camera is fixed.

The second camera 12 may come into focus only in a narrow range scale because the camera is generally scaled up significantly. However, depending on uses, a manual-focus lens is sufficient. That is the case when movement of the head is limited for a short time. For example, when a user or subject sits on a chair, the head will not move significantly if the position of seat is set. Since it is sufficient, in this case, to be in focus in a narrow range of about 10 cm, the camera becomes usable when the user or subject manually focuses the lens or a power-zoom lens is focused once by a handy switch or a remote control. If the camera is moved by body such as by hand or by a handy switch or a remote control in a system with an actuator and once adjusted in a direction and at a position where eyes' image can be taken, the camera becomes capable of measuring a line-of-sight. The aforementioned system can be produced at a comparatively low price. Also in this case, the three-dimensional position of a pupil is required as information for line-of-sight determination.

In addition, if the line-of-sight also needs to be detected even when the head moves significantly and a manual-focus lens or fixed-focus lens cannot be focused, an automatic-focus lens or power-zoom lens must be used. The automatic-focus lens is generally controlled by using images of the camera. If an image has high contrast, the image can be used for controlling, but if an image has low contrast due to such as an attached band-pass filter, a power-zoom lens can be used and controlled from outside.

In the aforementioned method, it was assumed that a relation between θ and |r| is linear and passes through the origin.

However, since an optical system and a visual axis of an eyeball are generally shifted slightly from each other, when a subject gazes at O, corneal reflection does not necessarily appear in the center of pupil image. That is, a visual axis does not necessarily pass through the origin. This situation must be corrected so that high-precision line-of-sight detection can be realized. As a corrective method, when calibrating a line-of-sight, it is necessary not only to make a subject gaze at a point somewhere, but also to measure |r| and φ' when the subject is made to gaze at O. That is, it is necessary to make the subject gaze at least at these two points to calibrate the line-of-sight.

In this case, after shifting r obtained when gazing at another point so that a vector r (shift component) connecting the center of corneal reflection and the pupil center obtained when making a subject gaze at O becomes a zero vector (origin correction), |r| and φ' are determined to perform calibration. Also in real-time line-of-sight detection, after making a similar correction of obtained r, |r| and φ' are determined and used to calculate the line-of-sight.

A three-dimensional view-point measurement device of the present invention determines the three-dimensional position of a view-point by determining a convergent point of the line-of-sights, as well as performing conventional detection of the direction of the line-of-sight. The present device is a non-contact line-of-sight detection device that can simultaneously detect the line-of-sights of both eyes without contact while allowing significant movement (for example, 30 cm) of the head forward and backward, or right and left from face images containing both eyes captured while illuminating the whole face with light sources provided near the aperture of two cameras apart from the face of a subject and capturing by these two cameras, and detects three-dimensional positions of two pupils by triangulation from the face images captured by the two cameras, further analyzes in detail surroundings of two pupils detected in each of two face images, and detects two precise pupil centers and two corneal reflection centers to detect the line-of-sights of two eyes. An intersection of these two line-of-sights is the view-point and three-dimensional view-point measurement can be performed.

Embodiment 1

Figure 9:
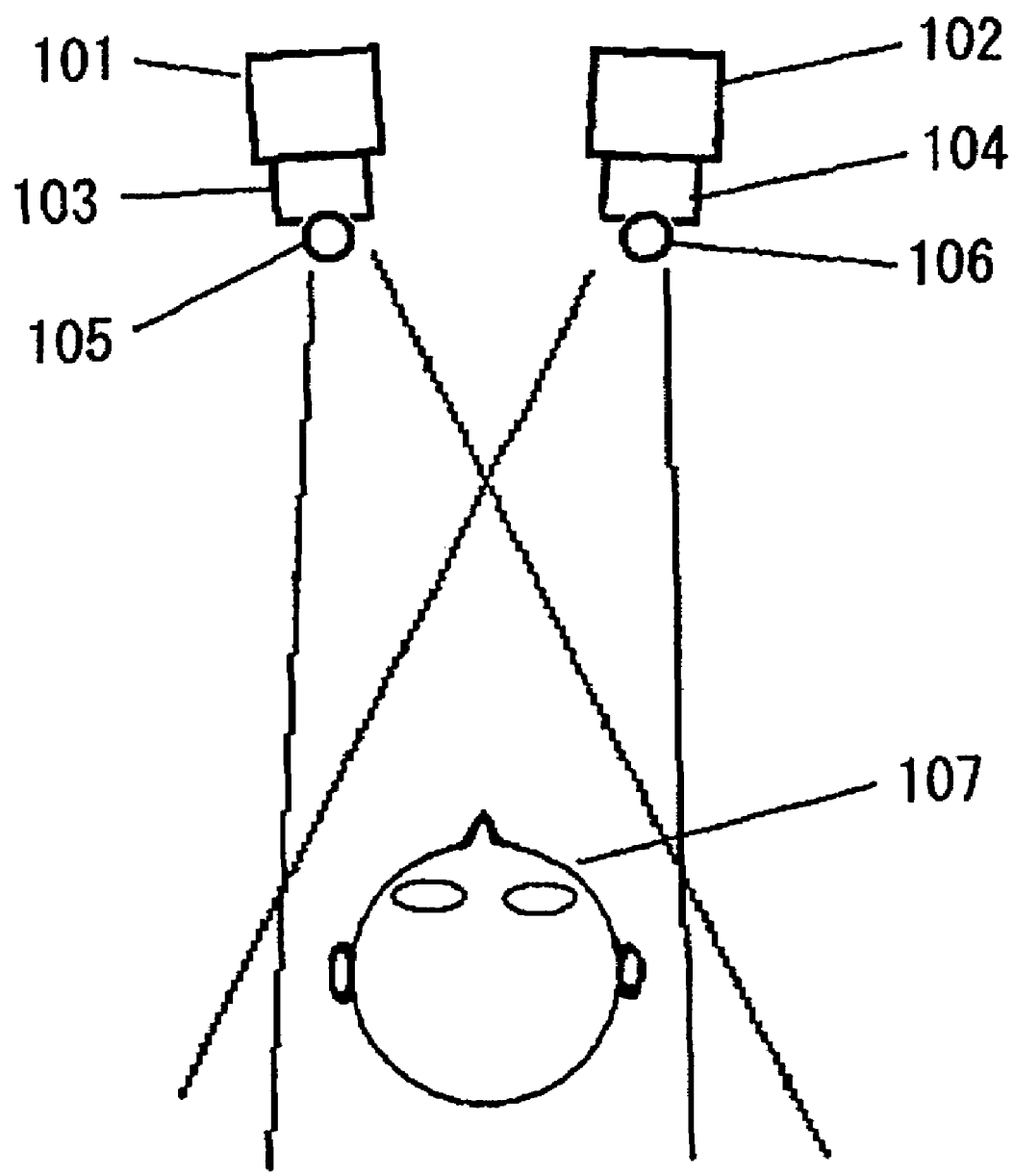
FIG. 9 is a diagram showing the arrangement of two cameras and a subject.

As shown in FIG. 9, two cameras (camera 101, camera 102) are placed apart from a face 107 of a subject and light sources 105 and 106 of the same wavelength are provided substantially inside an aperture or near the aperture of lenses 103 and 104 of these cameras to illuminate the whole face 107. The two cameras (camera 101, camera 102) are driven synchronously to turn on the light sources 105 and 106 mounted on the two cameras alternately in sync with an odd field and an even field.

Figure 11:
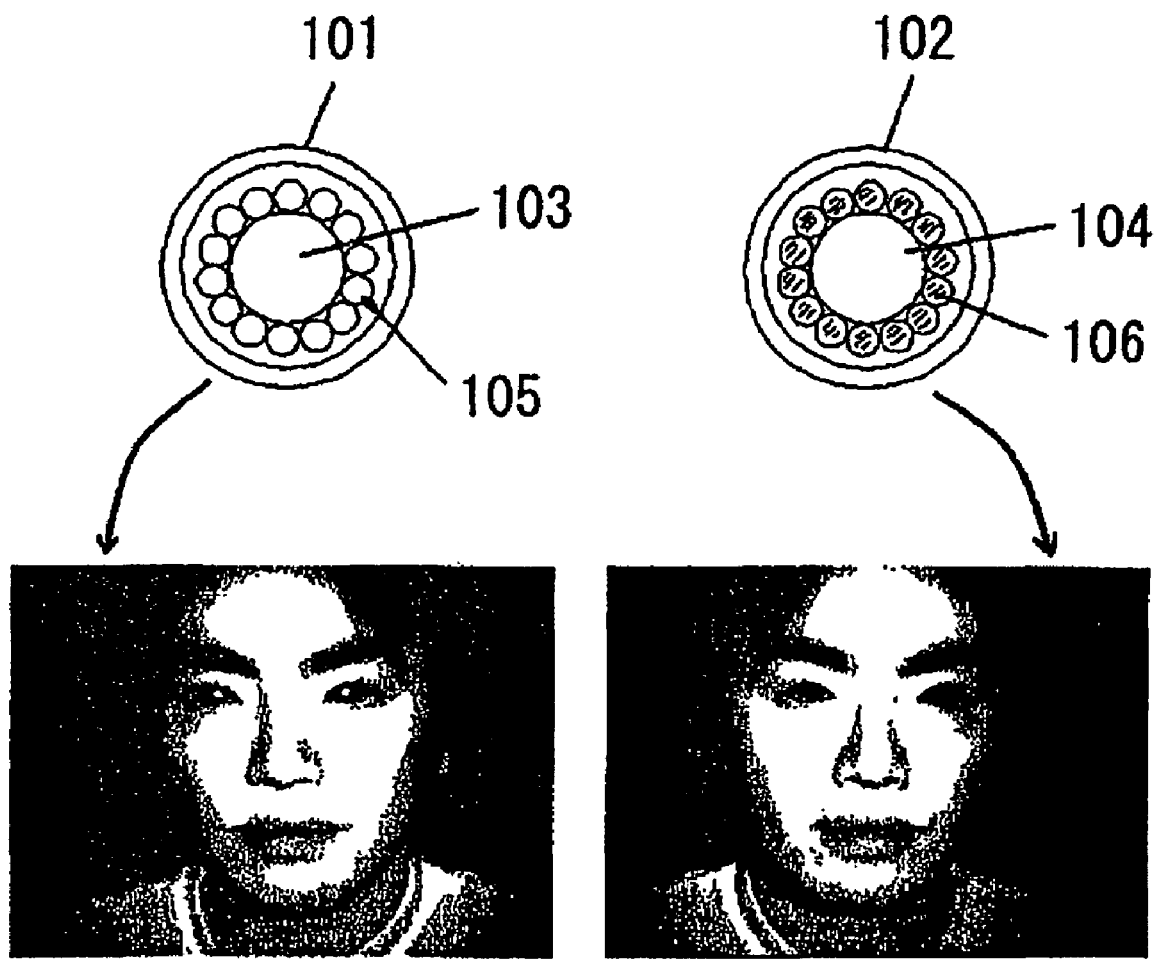
FIG. 11 is a diagram showing turning ON of a light source 105 and images of pupils of a subject.

As shown in FIG. 10, when the light source 105 mounted on the one camera 101 is turned on in the odd field, a phenomenon in which pupils are taken brighter than surroundings in images of the odd field of the one camera 101 occurs (bright pupil: FIG. 11 (left)), and another phenomenon in which pupil images are taken darker than surroundings in images of the odd field of the other camera 102 occurs (dark pupil: FIG. 11 (right)).

Figure 12:
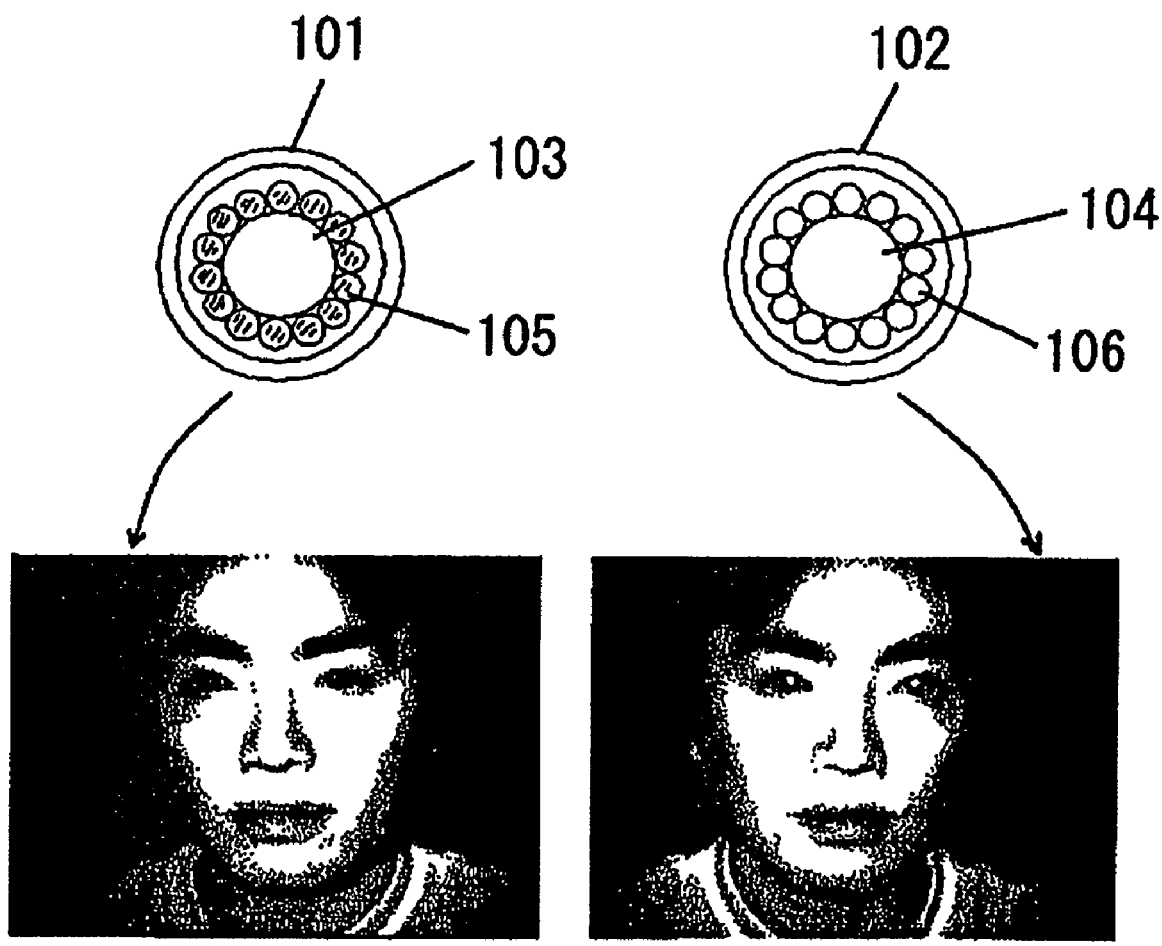
FIG. 12 is a diagram showing turning ON of a light source 106 and images of pupils of a subject.

Similarly, when the light source 106 mounted on the other camera 102 is turned on in the even field, dark pupils (FIG. 12 (left)) and bright pupils (FIG. 12 (right)) are observed in images of the even field of the one camera 101 and the other camera 102 respectively.

Since other parts than the pupils cancel out each other when an image difference is produced by basically subtracting dark pupil images obtained from each camera from continuous bright pupil images, only pupil parts can easily be detected.

To speed up pupil detection processing, in an initial image, approximate whereabouts of two pupils are detected by analyzing pixels at intervals in the whole image. Then, a window is provided around each of the detected approximate pupils (two squares in FIG. 13), and from the next frame onward, only images inside the windows are analyzed or only images inside the windows are captured from the cameras to shorten the time for image analysis.

Figure 14:
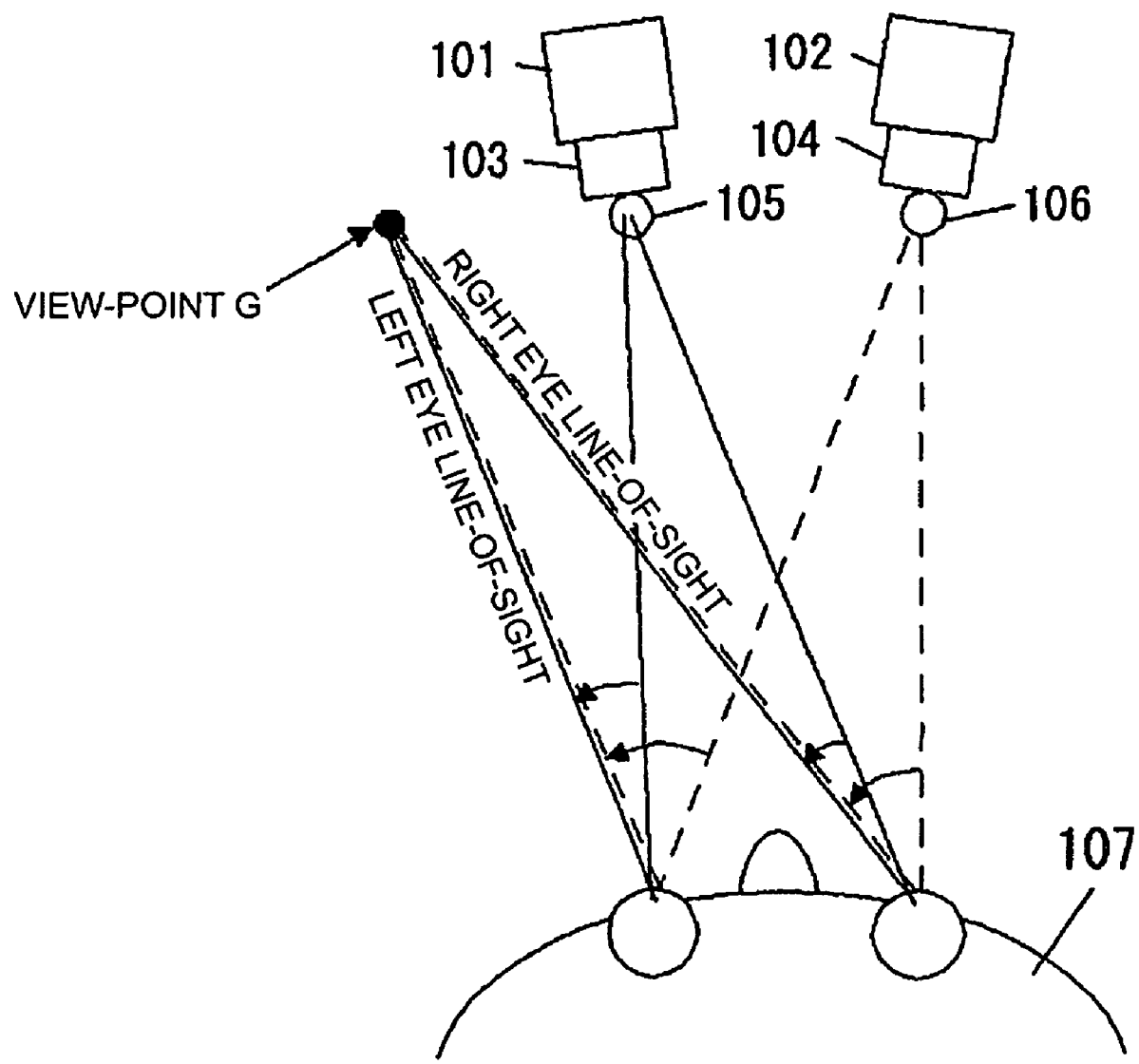
FIG. 14 is a schematic diagram for determining a viewpoint by line-of-sight detection of both eyes.

All pixels are basically analyzed in detail when analyzing images inside the two windows and the pupil centers and corneal reflection centers of both eyes are detected accurately to determine the line-of-sights (FIG. 14).

A CMOS sensor that is high-definition and capable of random access or window cutting is used as an image sensor to speed up data transmission from the image sensor to an image processing portion. This enables more frequent detection of coordinates of the pupil centers and corneal reflection centers. By applying a moving average of obtained line-of-sights or view-point data, they can be made more stable.

Furthermore, by shortening a time interval between two continuous images a difference of which should be produced, displacement of pupil image between two images are made more difficult to occur, contributing to improvement in the precision and detection rate of not only view-points and line-of-sights, but also three-dimensional pupil positions. This facilitates detection of pupils based on differences, and at the same time, substantially enables synchronization of two cameras even if the head moves and pupil images move quickly within a camera frame.

Incidentally, though two cameras are still used, other methods of improving synchronization shifts between cameras can yet be considered by, for example, increasing the number of light sources, using an optical filter, or making dedicated cameras.

Embodiment 2

Figure 15:
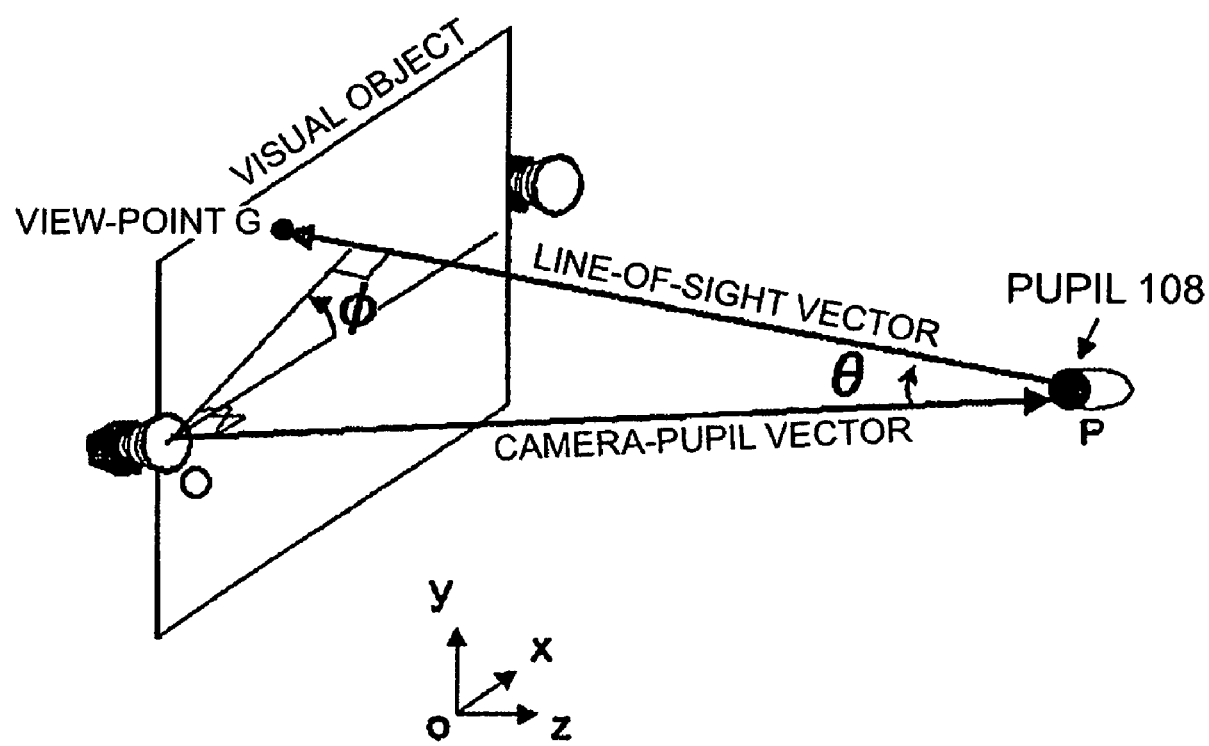
FIG. 15 is a diagram showing an association between a line-of-sight vector, and φ, θ.
Figure 16:
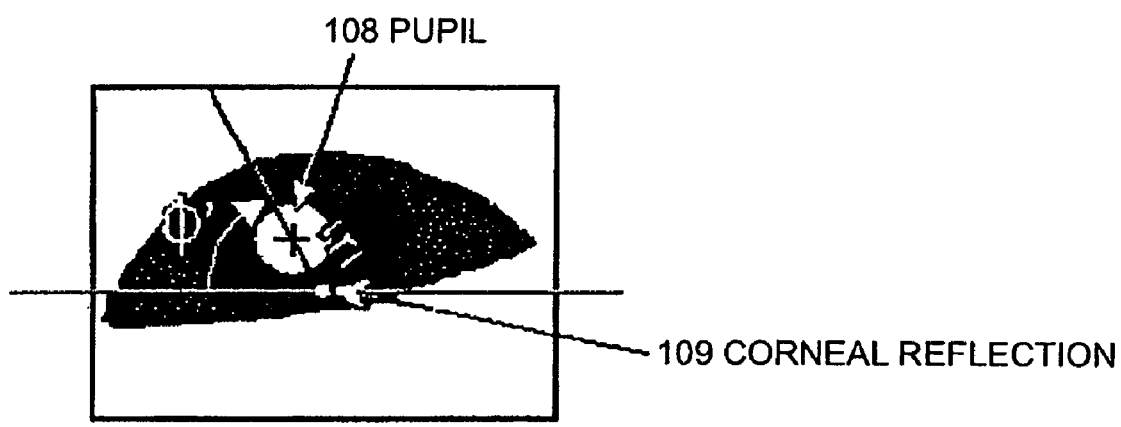
FIG. 16 is a diagram for determining a line-of-sight vector from a pupil center and a corneal reflection.

Each of the two cameras can basically detect the line-of-sights of both eyes. Now, as shown in FIG. 15, for the line-of-sight of one eye, three-dimensional coordinate of the pupil in the world coordinate system constructed when camera calibration of two cameras is performed is estimated from pupil coordinate obtained from the two cameras. Now, only the camera on the left is noticed. A camera-pupil vector in the world coordinate system is determined from three-dimensional coordinate of the pupil estimated and coordinate of the camera determined by camera calibration. If the line-of-sight vector is defined as a vector directed from the pupil to the view-point, the angle formed by the camera-pupil vector and the line-of-sight vector can be represented by θ and φ in the diagram, where θ is, in the range of about ±30 degrees, approximately linearly related to |r| of a vector r directed from the corneal reflection center to the pupil center in the image shown in FIG. 16 (θ=k|r|, where k is a constant). φ is also related to φ', which indicates the direction of r, like φ=φ'. The view-point G is determined as an intersection of the line-of-sight and the visual object.

If the plane where the visual object exists is unknown, an intersection of the line-of-sight vectors of both eyes is the view-point G.

In the above processing, since the line-of-sight vector of one eye can be obtained from each of the two cameras, an average vector of these vectors may be defined as the final line-of-sight vector. If corneal reflection disappears when θ becomes larger and, instead, a white part of the eye starts to shine, virtually making it impossible to detect a line-of-sight from a relative position relation of the pupil center and the corneal reflection center (for example, when viewing to the right of the camera on the right in FIG. 15), a method must be devised such as using only a line-of-sight vector determined by the right camera because it is difficult to detect the line-of-sight using the left camera.

When viewing further to the right, even the right camera cannot detect corneal reflection. In this case, an approximate direction of the line-of-sight is detected from ellipticity of the pupil. If θ>30° or corneal reflection cannot be detected for some reason (for example, when spectacle reflection or eyelashes overlap corneal reflection), ellipticity shall be used. Though a method of using ellipticity is problematic in view of precision as mentioned above, this method is effective when viewing in a direction sharply deviating from the front and no precision is needed.

A reason why the line-of-sight direction can be detected from relative coordinates of the corneal reflection and pupil centers is described below.

<Characteristics of Corneal Reflection>

Figure 19:
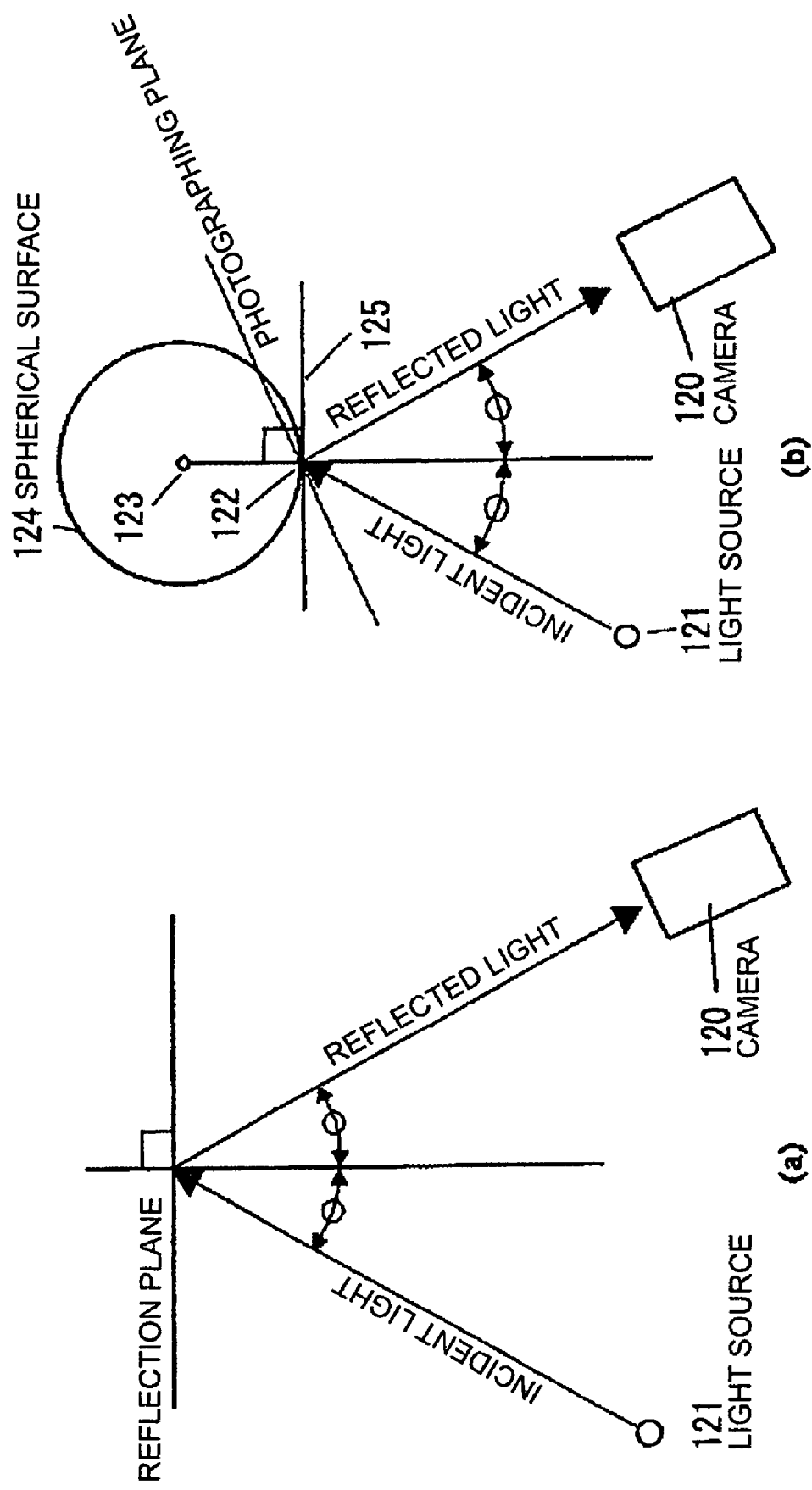
FIGS. 19(a) and 19(b) are diagrams showing the reflection law.

Corneal reflection is represented as shown in FIG. 19 (left) because the incident angle and reflection angle are the same when light emitted from a light source 121 (point light source) is reflected by a reflection plane to enter a camera. If, here, the object is not a plane, but a spherical surface, the situation can be represented as shown in FIG. 19 (right). In this case, when viewed from a camera 120, the light source 121 appears as if it were at a contact point 122 of a tangent plane 125 of a spherical surface and a spherical surface 124. The incident angle and reflection angle are equal relative to a straight line connecting a center 123 of the spherical surface and the contact point 122.

Figure 20:
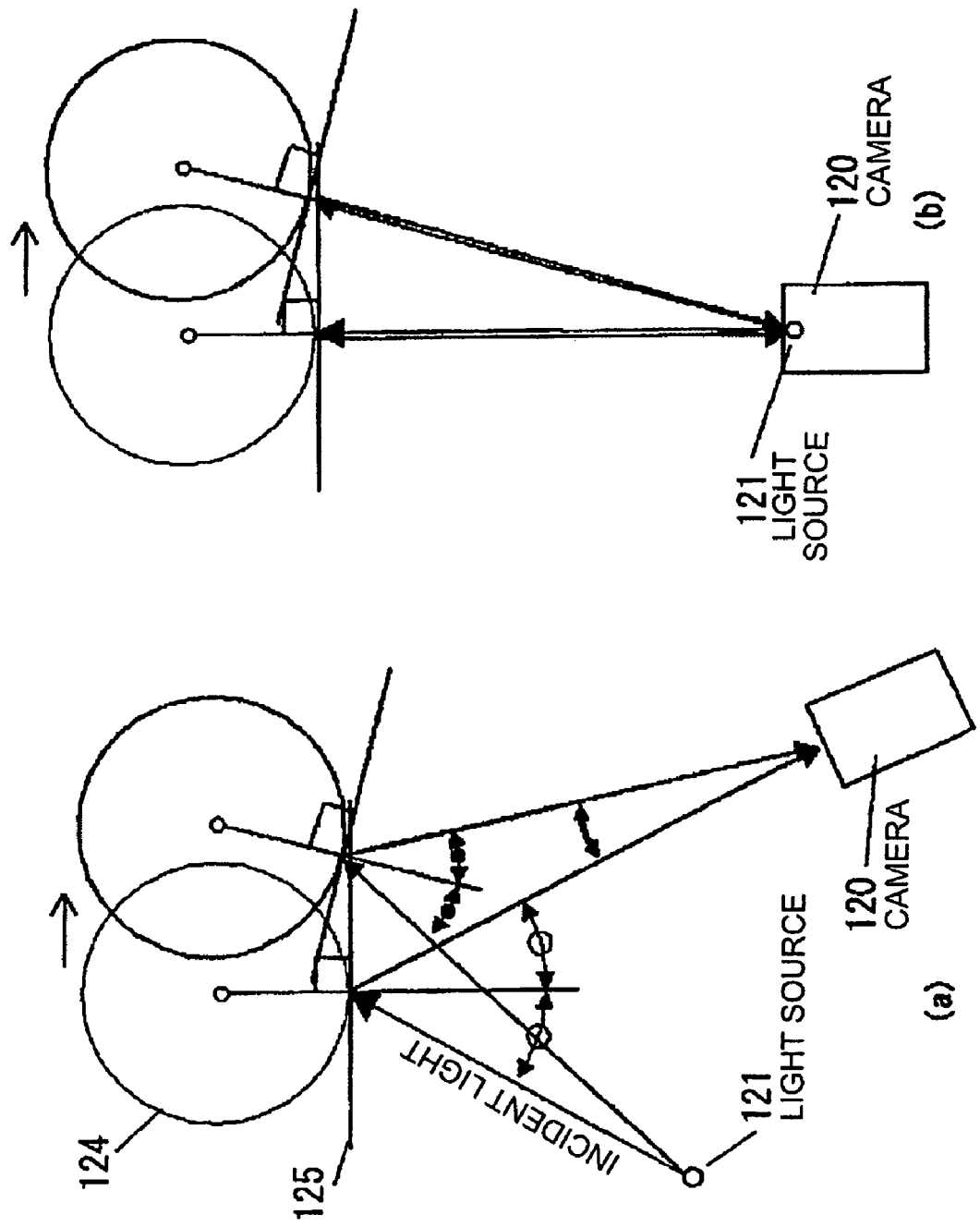
FIGS. 20(a) and 20(b) are diagrams showing the cases in which a spherical surface moves in a lateral direction relative to a camera and a light source.

Here, if the spherical surface (cornea of an eyeball) moves in space relative to the camera 120 and the light source 121, as shown in FIG. 20 (eft), reflection of the light source 121 moves in the image when viewed from the camera 120 because the visual angle from the camera changes. As described above, if the spherical surface is considered typically as a corneal spherical surface, it is apparent that a corneal reflection image moves in the image as the cornea moves due, for example, to movement of the head. Furthermore, if the position of the light source 121 or the position or direction of the camera 120 is different, it can easily be imagined that the position of corneal reflection image varies in the camera image.

Figure 21:
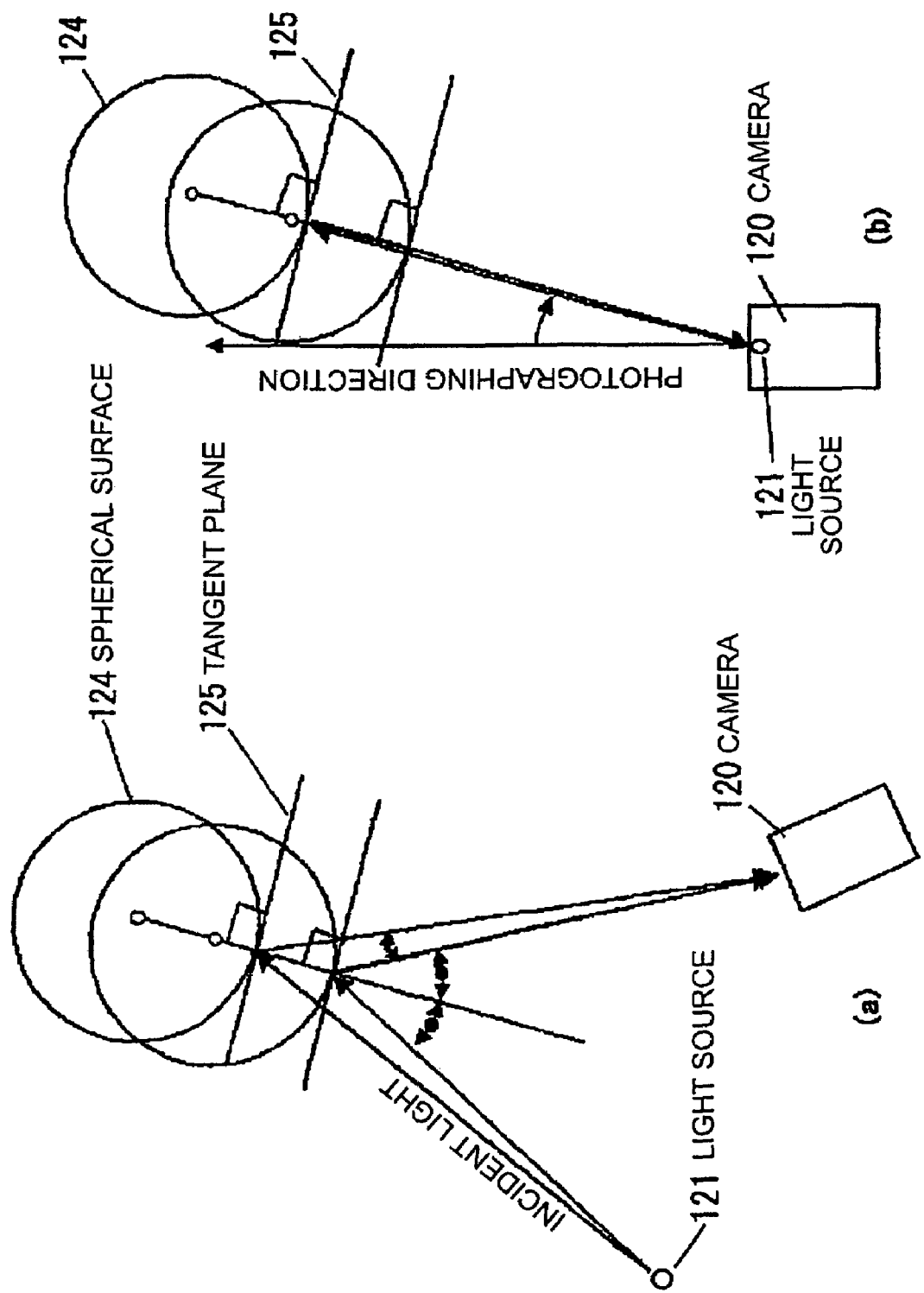
FIGS. 21(a) and 21(b) are diagrams showing the spherical surface moving in a depth direction.

Now, the case is considered in which the position of the light source and that of the camera agree (FIG. 20 (right)). In this case, a beam directed from the light source to the spherical surface and that returned from the spherical surface to the camera agree. Such a condition is superior to the case in which the light source and the camera are at different positions. This is because, if the position of the light source and that of the camera do not agree, as shown in FIG. 21 (left), a corneal reflection image moves in the image when moving in the depth direction relative to the light source and camera, but if they agree (FIG. 21 (right)), when the corneal sphere moves at a fixed angle relative to a photographing direction of the camera, a corneal reflection image is advantageously taken at the same position in the image. Therefore, if the position of the light source and that of the camera agree, only rotation of surroundings of the camera (light source) causes a problem about the corneal reflection image.

<A Reason Why the Angle Formed by the Camera-pupil Vector and the Line-of-sight Vector is Known from the Size |r| Between the Corneal Reflection Center and the Pupil Center in a Photographed Image and a Method Thereof>

Figure 22:
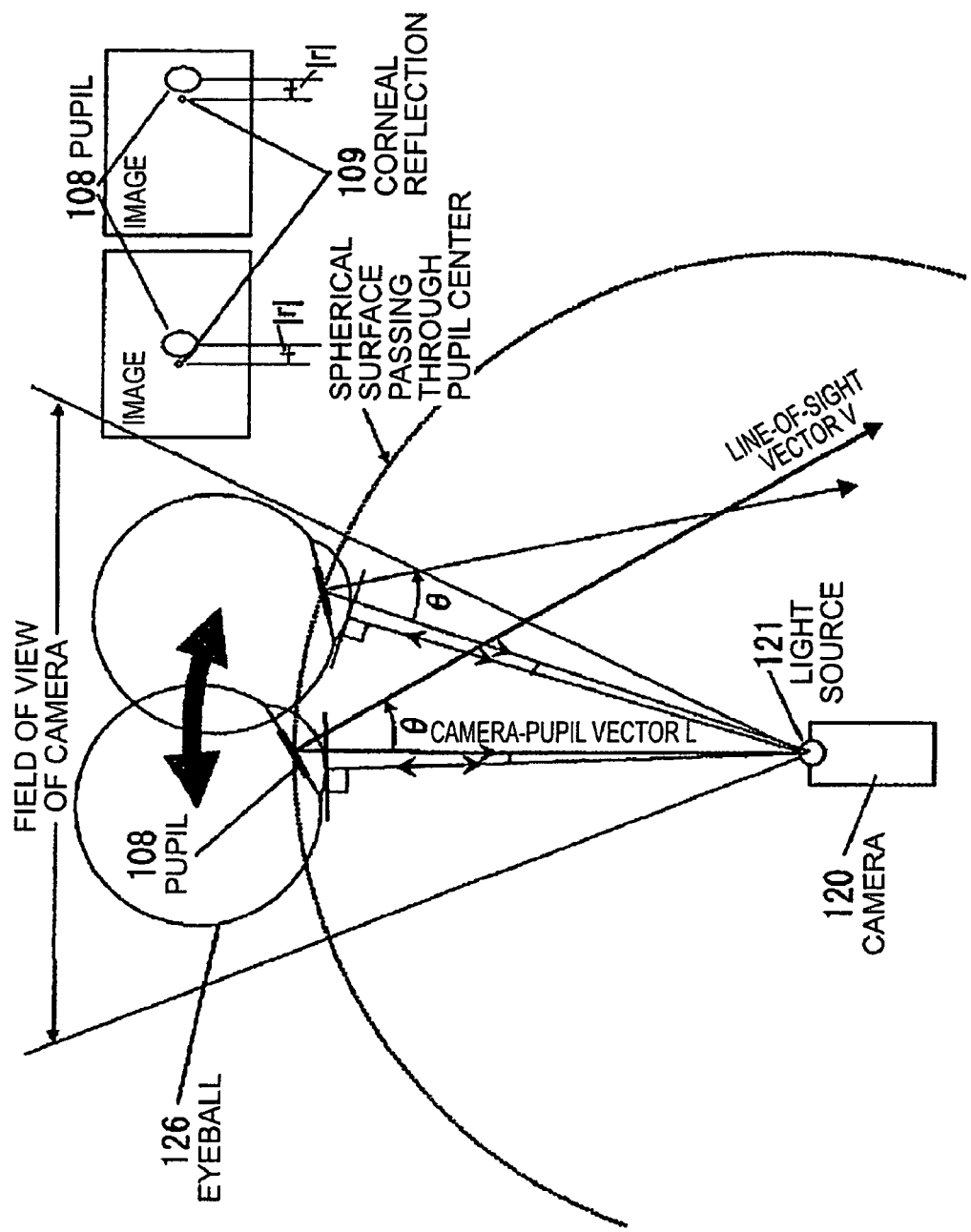
FIG. 22 is a diagram showing a pupil moving by maintaining a constant distance from the camera and light source.

It is assumed, as shown in FIG. 22, that an eyeball moves within a field of view of a camera for line-of-sight detection. Since the three-dimensional position of the pupil is known with a stereo camera, it is assumed that the pupil moves while maintaining the distance to the camera and light source constant. At this point, it is however assumed, that the angle θ formed by the camera-pupil vector and the line-of-sight vector does not change while moving. Here, however, in the interests of simplicity, it is assumed that the pupil (eyeball) moves on a horizontal axis of the camera. It is to be noted at this moment that the physical relationship between a corneal reflection image and a pupil image viewed from the camera does not change at all. When the pupil moves on a circumference around the camera (lens, light source), a relative distance between the corneal reflection image and the pupil image in the image does not change.

Figure 23:
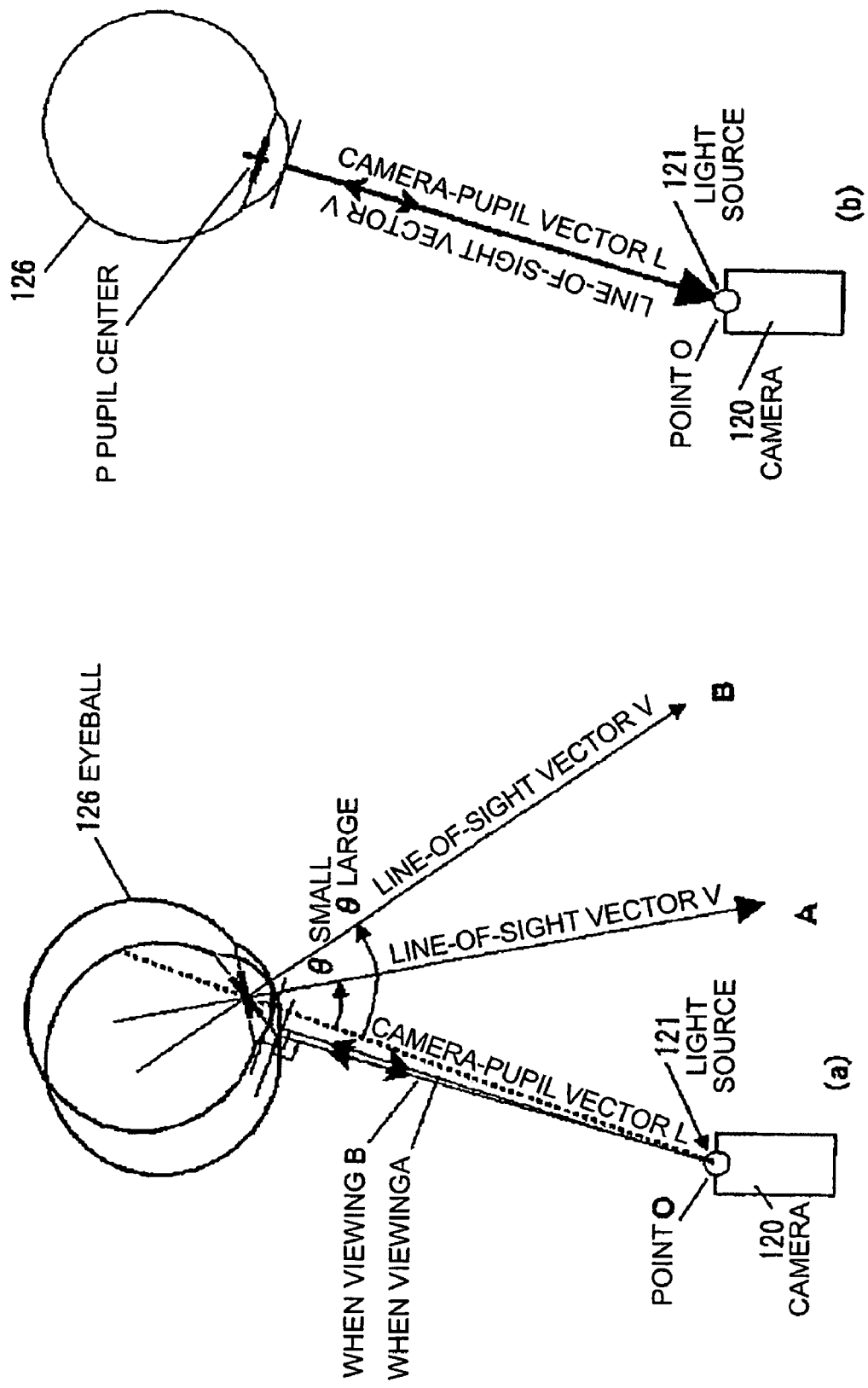
FIGS. 23(a) and 23(b) are diagrams showing the relationship between a change of the line-of-sight vector and the corneal reflection when the position of the pupil center is fixed.

On the other hand, the case is considered, as shown in FIG. 23 (left), in which the starting points of the line-of-sight vectors are the same (the same three-dimensional position of the pupil), but the direction vectors are different. In this case, as shown in the diagram, the position of corneal reflection changes. It is apparent that, when viewed from the camera, as the angle formed by the line-of-sight vector relative to the camera-pupil vector increases, that is, θ increases, the size |r| between the cornea reflection center and the pupil center in the image increases. As FIG. 23 (right) shows, when the eye is directed to the camera, the corneal reflection center is essentially positioned at the pupil center and |r|=0.

Figure 24:
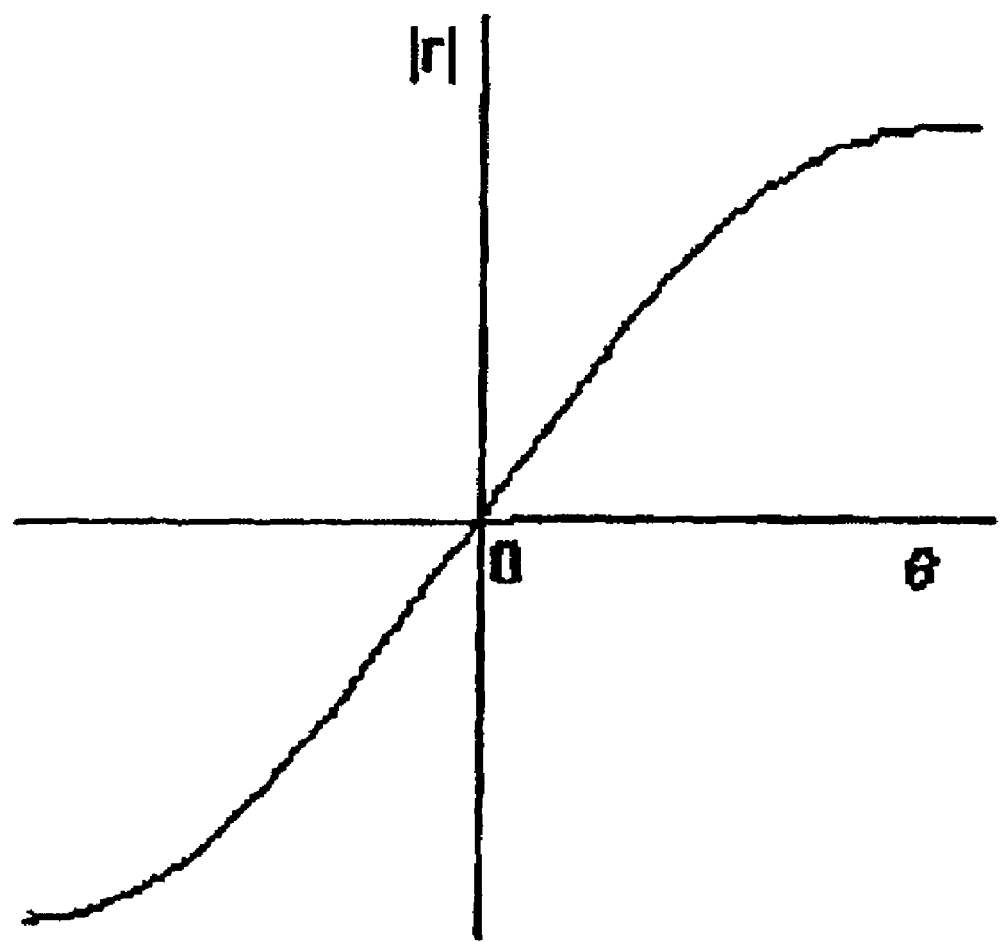
FIG. 24 is a diagram showing the relationship between the angle θ formed by a camera-pupil vector and the line-of-sight vector and a size |r| of a corneal reflection center-pupil center vector r in a camera image.

Therefore, there is a simply increasing relation passing through the origin shown in FIG. 24 between the angle θ formed by the camera-pupil vector and the line-of-sight vector and the size |r| of the vector r from the corneal reflection center to the pupil center. This relation depends on the subject due to a difference of the optical system of the eyeball. Determining the θ–|r| relation can be said to be calibration of the line-of-sight of the present technique. Furthermore, since there is normally a shift between the optical axis and visual axis of the optical system of the eye, the above relation needs to be corrected because the origin is not necessarily passed through. These points will be described later.

In both of FIG. 23 (right) and FIG. 23 (left), it is to be noted that θ and |r| do not change when only the direction (photographing direction around the point O) of the camera changes. Therefore, information on the direction of camera is not needed and simply a pupil and corneal reflection need to be taken in a camera frame. Moreover, as described using FIG. 22, a fact that |r| still remains constant is reemphasized even when the eyeball moves around the point O, as long as the distance from the point O to the pupil center P is maintained constant while maintaining θ constant.

Figure 25:
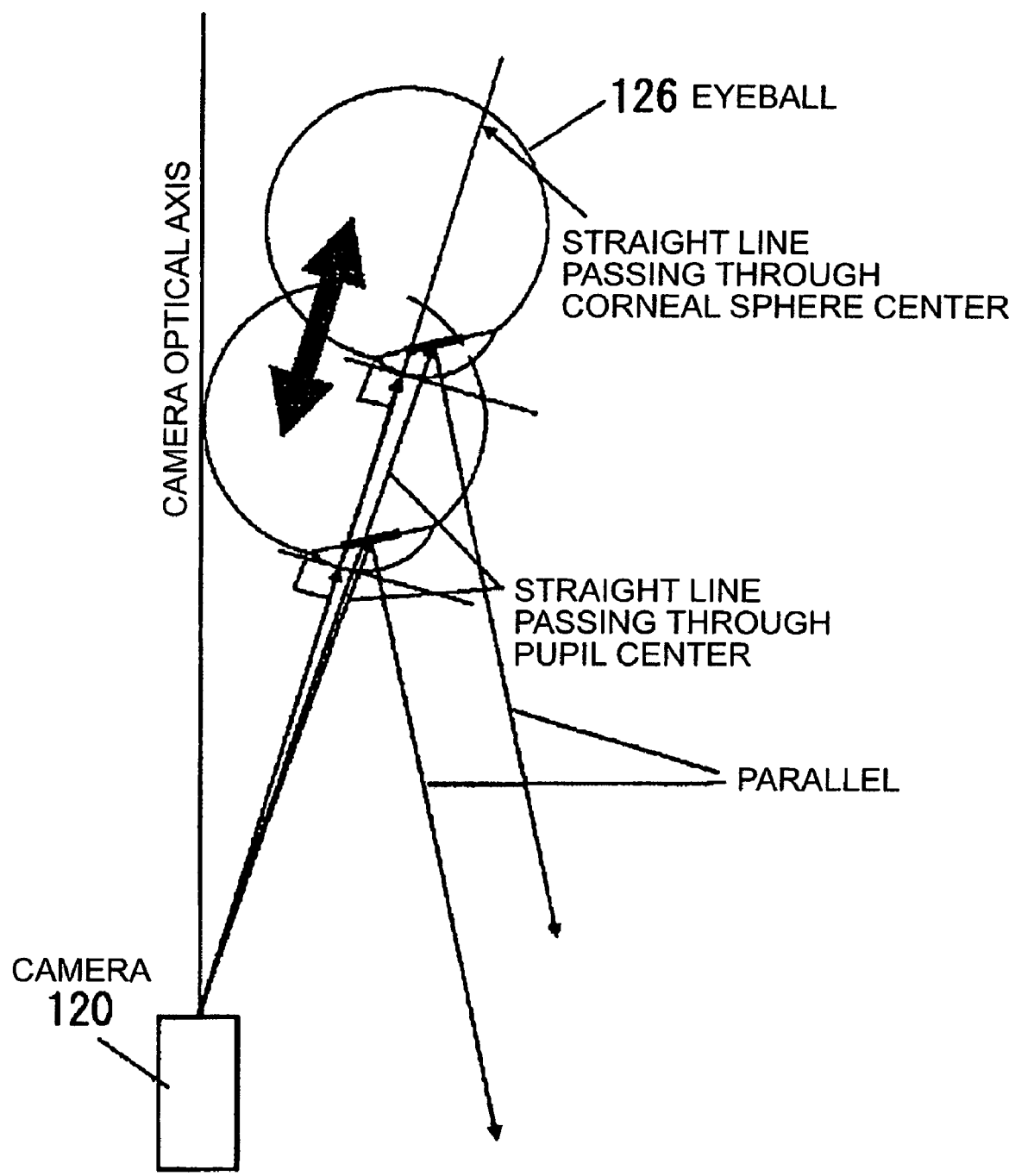
FIG. 25 is a diagram showing an effect of a change in the distance between the camera and the pupil center on |r|.

However, if the distance (OP) between the point O of the camera position and the pupil center P changes, |r| changes even though θ does not change. This is because, if the camera lens is a fixed-focus lens, as the distance between the camera and an object increases, the object taken as an image becomes smaller. Thus, this situation must be corrected. The correction is considered by using the fact that, as described above, the same θ–|r| relation is always realized regardless of the angle formed by the camera-pupil vector and the optical axis of the camera. Now it is assumed that, to facilitate illustration, the pupil exists at a position where, though the distance from the camera to the pupil center changes, the direction of the line-of-sight does not change, as shown in FIG. 25. As is evident from the diagram, when the distance viewed from the camera changes, the size |r| between the pupil center and corneal reflection center taken by the camera changes (In this case, coordinate of the pupil center in the image naturally change. However, this needs not to be considered and it is sufficient to focus on a relative position relation between corneal reflection and the pupil center.).

Figure 26:
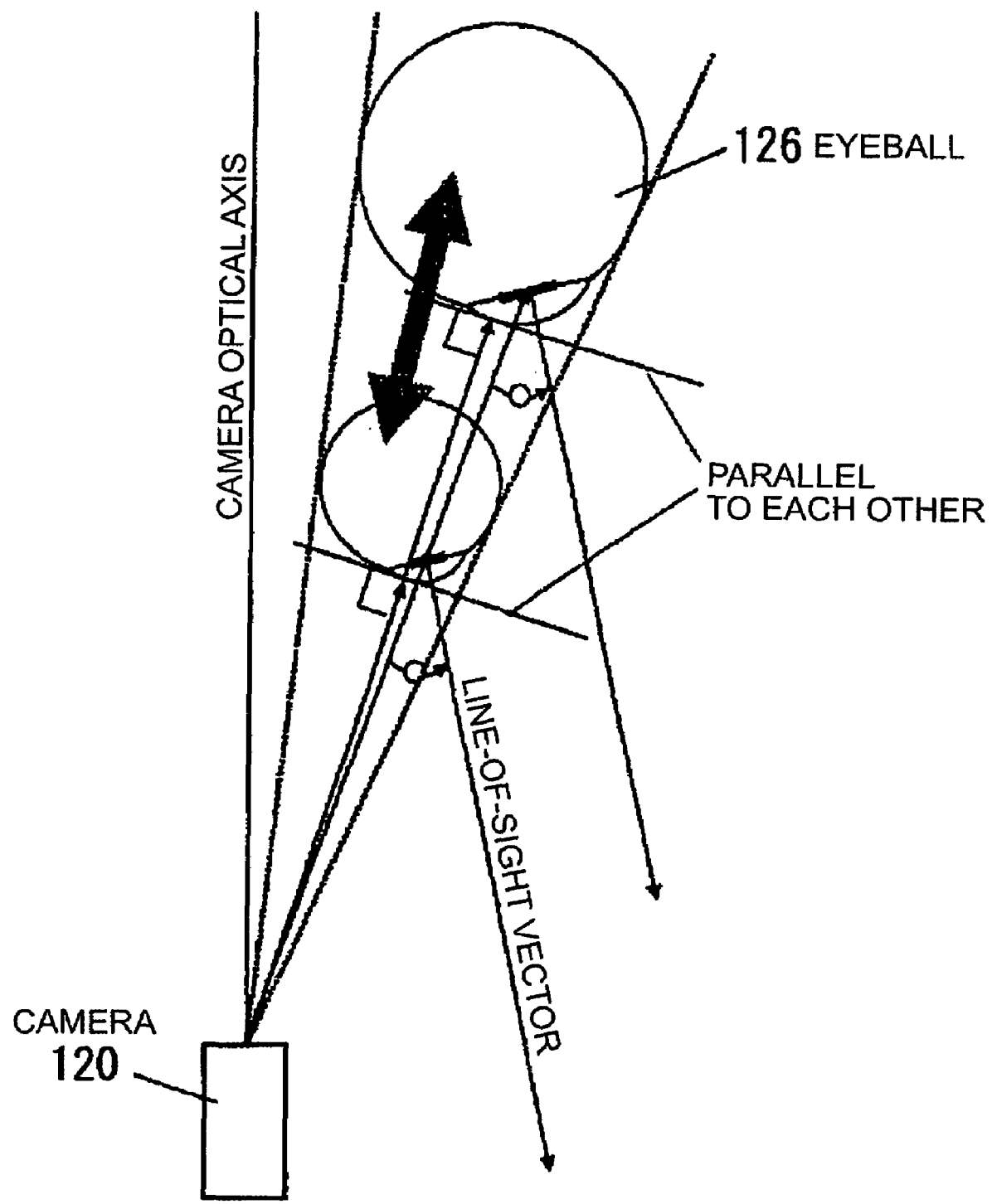
FIG. 26 is a diagram showing an example in which a correction is made so as to change the size of an eyeball in accordance with the change in the distance between the camera and the pupil center.

Now, it is however assumed that, because |r| changes due to a change of the distance OP, as described above, a camera exists that corrects this situation and always takes an object with the same size. If, a s shown in FIG. 26, the object (here an eyeball) is drawn by changing the size thereof depending on the distance OP, |r| can be maintained constant independent of the distance OP. For a fixed-lens camera that cannot take an object with the same size when the distance changes, |r| in the image may be corrected depending on the distance. However, a relation between the distance OP and |r| for correction must be examined in advance. In contrast to calibration of the line-of-sight, however, this is a kind of camera correction and has nothing to do with a subject. Here, OP is calculated from the P coordinate determined by the stereo camera.

In addition, in FIG. 25, an optical path connecting the light source and the pupil center is actually not a straight line, but is refracted at a boundary surface between air and the front of cornea and at a boundary surface between the back of cornea and aqueous humor. As is evident from FIG. 25, as the distance OP changes, the optical path connecting the light source and the pupil center changes and the changed path passes through a different corneal position. Since the incident angle of light to the boundary surface changes depending on the corneal position, the refraction angle at the boundary surface also changes. Therefore, even if the aforementioned camera correction is made, |r| is still subtly affected by the distance OP. |r| is corrected by using, for example, refractive index and cornea curvature radius information of the standard human cornea and aqueous humor, as required.

<Angle ($\phi$) of the Line-of-sight Vector Around the Camera-pupil Vector and Calibration of the Line-of-sight>

Incidentally, $\phi$ must be clarified, in addition to $\theta$, to determine a line-of-sight vector. However, as described above, $\phi$ and the angle $\phi'$ formed by the vector r directed from the corneal reflection to the pupil center in the image and the horizontal axis (axis of abscissas in FIG. 16) of the camera must basically be equal.

Thus, it is suggested that no calibration is needed for the angle ($\phi$) of the line-of-sight vector around the camera-pupil vector. If this assumption is correct and the $\theta$–|r| relation shown in FIG. 24 is linear and passes through the origin, it becomes possible to perform line-of-sight calibration by only making a subject gaze at a point somewhere.

Embodiment 3

With capabilities of simultaneously measuring the line-of-sights of both eyes, it becomes possible to measure an angle of convergence (angle formed by the line-of-sights of both eyes) and a view-point in the depth direction (intersection of the line-of-sights of both eyes), indicating the distance to an object being gazed at. As a result, the view-point in three-dimensional space can be known.

This suggests an application to evolved 3D display and the like. If the eyes are not focused on a normal 3D display, it is not possible to view clear images. Thus, a watcher is forced to watch in an unnatural way against the normal human visual function that the eye focus does not change when the angle of convergence changes. However, by using an evolved 3D display that, even if the focus is shifted in the depth direction, comes into focus accordingly, more natural three-dimensional visual appreciation will be experienced.

In this type of display, by providing spatial positions of the eyes and focal positions of the eyes, the display can be adjusted so that images can selectively be displayed accordingly in a direction of two eyes, and at the same time, the focal positions of the eyes actually come into focus. Information (three-dimensional positions of two pupils and point of intersection of the line-of-sights of both eyes, 3D view-point) required for such adjustments can be obtained from the present system. Three-dimensional pointing using the line-of-sights also becomes possible.

That is, in a normal 2D display and view-point mouse by one eye, the view-point mouse is simply used for selecting windows arranged on a two-dimensional plane, but in the above-described full-scale 3D display, windows are arranged in 3D space and a window hidden behind can immediately be displayed on top of other windows by a three-dimensional view-point. In this way, the present system can also be used for three-dimensional pointing.

Embodiment 4

With the configuration described above, three-dimensional positions of two pupils can be measured. The pupil is the source of a line-of-sight and shows from where a user is gazing (not where a user is gazing at).

Figure 17:
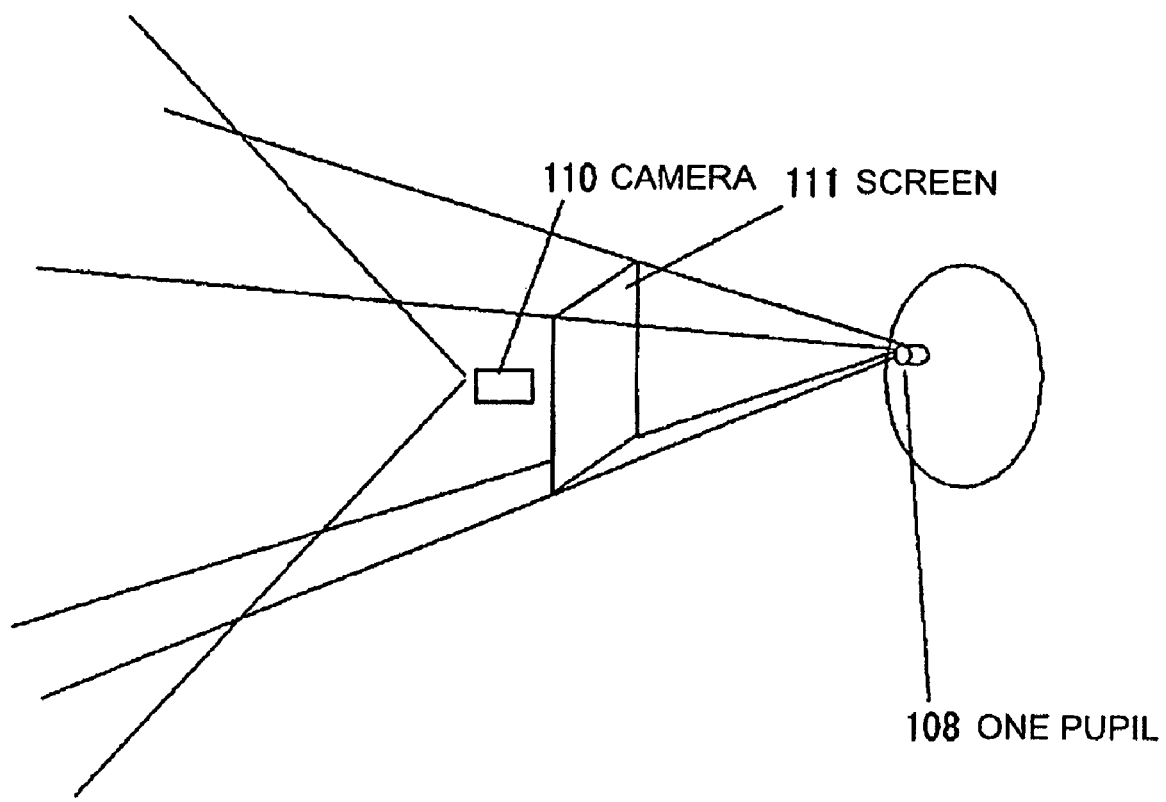
FIG. 17 is a schematic diagram for detecting a three-dimensional position of a pupil and controlling the size and position of an image to be shown on a screen.

As an application, it is supposed that there is a screen and a wall in front of a user in a virtual reality or actual world, and it is not possible to view beyond the screen (FIG. 17). However, it is supposed that a camera to take images displayed on the screen is placed beyond the screen and there is the wall where there is no screen.

Figure 18:
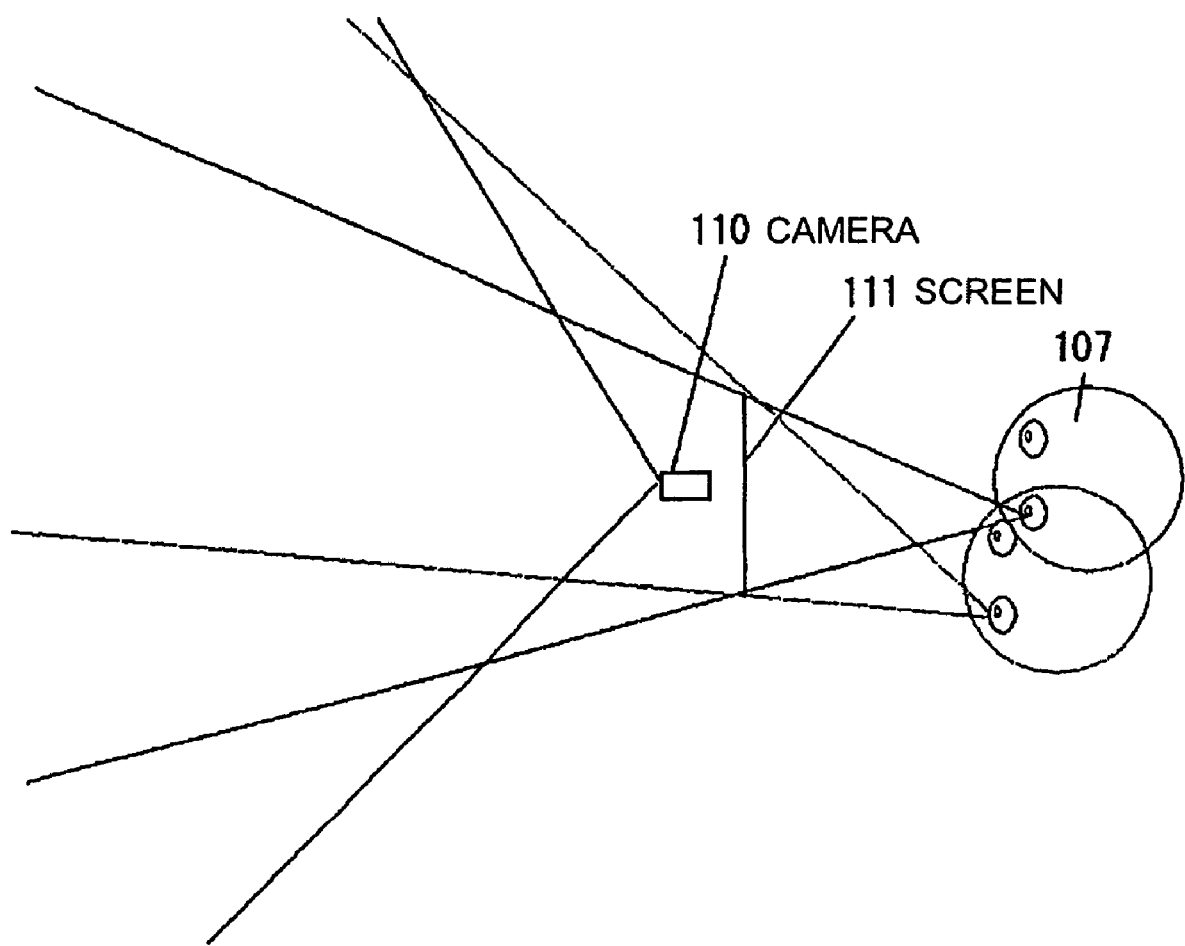
FIG. 18 is a diagram showing how a field angle of an image changes as the position of a pupil changes.

At this point, the screen can be caused to operate as if the screen were a window and outside of the window were viewed. Namely, if the head moves (FIG. 18), part of images taken by a wide-angle camera is caused to be displayed on the screen accordingly. In this way, required images can be displayed in a form full of such realism.

In the concept of "Pointing system by pupil movement" proposed by the present inventors, movement of a pupil within the camera frame is simply caused to be reflected in cursor movement, but according to the present system, since the three-dimensional position of a pupil is known, movement of the head in the depth direction relative to the screen can be caused to be reflected.

Arrangement of the screen and camera depends on application. In any case, in an image that is displayed by enlarging it, parts that are hidden behind and invisible can be seen by moving the head as if peeping out of the window. Thus, an image to be displayed on the screen does not have to be always an object nearby, and an object in the distance or a micro-object taken by enlarging it may be acceptable. Parts to be seen can be changed by moving the head right and left, or up and down (rotation is also permissible), and further by moving the head forward and backward, the zoom ratio is significantly changed so that an object can be seen from a favorite angle with a desired zoom ratio.

Therefore, when used in combination with a PC, if a three-dimensional object (for example, a molecular model) is displayed on the PC screen and to be seen by rotating it, a mouse for a desktop computer is normally used, but by using the present device, the object can be freely moved in a natural atmosphere only by rotating or translating the head.

According to the present system, if unchanged, the same image will be seen by both eyes. If this is inconvenient, images of different cameras may be caused to enter the right and left eyes by using a 3D display and two cameras.

Embodiment 5

The present application is useful in an environment where something should be hidden from other people such as a security system. For example, to make the display invisible to other people even if they look into when using an ATM system or the like in a bank, the present method can be used to control the display so that the display is visible only from the two pupil positions of the user or a nearby direction.

Similarly, to do PC work that should not be glanced at when other people are present around (for example, in Shinkansen), by combining a display that can make content visible only from a specific direction with the present method, the content can be made visible only to a person who operates the PC.

For the above purposes, a display unit such as a liquid crystal display that has a narrow angle of visibility and can be controlled is suitable.

The present method has another advantage. Because the display can be made to have a strong directivity, strong light can be sent into the eye while reducing power consumption.

Embodiment 6

Further, a field of electronic books can be considered as another embodiment. An advantage of the electronic books is that, by using a dedicated device, a page can be turned only by one button click. However, a manual operation is still needed. By combining such a dedicated device for electronic books with view-point detection means, for example, when the view-point moves significantly in a vertical writing text from left to right, the page can be caused to be automatically turned. Or, by providing a button area for page turning at a lower left corner of the screen or device, the page can be caused to be automatically turned when the view-point is aligned with the button area. Using such a device, it becomes possible to read a book without using a hand while lying in a bed or the like. This makes reading more comfortable and further increases advantages of electronic books. This will make very effective means for four limbs paralytics. The view-point detection means of the present invention can be made compact and such an embodiment can be carried out easily.

Here, the description has assumed a dedicated device for electronic books to be combined with the view-point detection means, but the means is still valid for notebook computer usage, and by embedding two cameras around a liquid crystal display, the line-of-sight can be used for selecting an active window or moving a high-speed mouse using the line-of-sight of the user.

INDUSTRIAL APPLICABILITY

A line-of-sight detection method and device of the present invention can be widely used in the field of monitoring human behavior or as line-of-sight input means in a human life environment or work environment. Application will be planned in the field of manufacturing electronic devices and in an environment of using electronic computers.

The three-dimensional view-point measurement device of the present invention has the applicability shown below:
1. With capabilities of simultaneously measuring the line-of-sights of both eyes using at least two cameras and two light sources, it becomes possible to measure an angle of convergence (angle formed by the line-of-sights of both eyes) and a view-point in the depth direction (intersection of the line-of-sights of both eyes), indicating the distance to an object being gazed at. As a result, the view-point in three-dimensional space can be known (point of intersection of the line-of-sights of both eyes, 3D view-point).
2. Three-dimensional positions of two pupils can be measured. A pupil is the source of a line-of-sight and shows from where a user is gazing (not where a user is gazing at). Therefore, the device is effective in a system in which from where being gazed at must exactly be known.
(Conventionally, this has had to be realized by attaching a magnetic sensor or the like to the head and measuring movement of the head, but whereabouts of pupils could not be exactly measured, in addition to attachment of a sensor to the head)
3. The present system is easy to realize because it has no actuator and two cameras are fixed.

If the camera has high sensitivity, the aperture of the camera can be made smaller, and the light source can easily be made compact by producing high-intensity light sources.
4. Because the line-of-sight can be detected by both of two cameras, the line-of-sight precision can be further improved by processing such as averaging detection results obtained from these cameras.

The invention claimed is:

1. A line-of-sight detection method of a subject using:
a first camera for measuring the position of a pupil relative to a coordinate system; a second camera having a light source arranged at a known position in the coordinate system and forming a corneal reflection center to obtain data of a size of vector r from the corneal reflection center to a pupil center and an angle $\phi$ of the vector r relative to a coordinate axis of the coordinate system; and a calculation means for calculating the line-of-sight direction for executing steps below based on information from each of the cameras, comprises the stages of:
determining a relational formula, including the steps of:
obtaining data on a coordinate point O of the position of a pupil of a subject with the first camera by making the subject gaze at a known point G in the coordinate system;
obtaining, in the state of the subject, data of the corneal reflection center, a size of vector r from the reflection center to a pupil center P, and an inclination $\phi$ of the vector r relative to the coordinate axis with the second camera;
calculating an angle $\theta$ between a line connecting a reference position of the second camera and the pupil center and a line-of-sight of the subject by the calculation means; and
calculating a formula $\theta=f(r^*)$ showing a relationship between $r^*$ related to r and $\theta$ based on the measured values and calculated value; and
determining a line-of-sight, including the steps of:
obtaining data on a coordinate point O' of the pupil position of the subject with the first camera by making the subject gaze at an unknown point G' in the coordinate system;
obtaining data of the corneal reflection center, a size of vector r' from the reflection center to the pupil center P, and an inclination $\phi'$ of the vector r' relative to the coordinate axis with the second camera; and
calculating $\theta=f(r^{*\prime})$ by using the relational formula to obtain the unknown point G' from the inclination $\phi'$ and $\theta'$.

2. The line-of-sight detection method of the subject according to claim 1, wherein $r^*$ is r itself or a corrected value of r based on OP, and $r^{*\prime}$ is r' itself or a corrected value of r' based on OP'.

3. The line-of-sight detection method of the subject according to claim 1, wherein the first camera is a stereo camera arranged by aligning a baseline in a horizontal axis direction of the coordinate system, and a light source of the second camera is constructed so as to provide an optical axis that is substantially aligned with that of the second camera.

4. The line-of-sight detection method of the subject according to claim 1, wherein the first camera is a stereo camera, and a light source of the second camera is constructed so as to provide an optical axis that is substantially aligned with that of the second camera.

5. The line-of-sight detection method of the subject according to claim 1, wherein the formula $\theta=f(r^*)$ showing the relationship between $r^*$ and $\theta$ is given by $\theta=k\times r^*$ (where k is a constant).

6. A line-of-sight detection method of the subject according to claim 1, wherein the pupil is one of pupils of the subject.

7. An line-of-sight detection device of the subject, comprising:

a first camera for measuring a position P of a pupil relative to the coordinate system;

a second camera having a light source arranged at a known position in the coordinate system to obtain data of a size of vector r from a corneal reflection center to a pupil center illuminated by the light source and an angle $\phi$ of r relative to the coordinate axis; and a calculation means for executing the steps of:

obtaining data on a coordinate point P of the position of a pupil of a subject with the first camera by making the subject gaze at a known point G in the coordinate system;

obtaining, in the state of the subject, data of the corneal reflection center, a size of vector r from the reflection center to a pupil center P, and an inclination $\phi$ of the vector r relative to the coordinate axis with the second camera;

calculating an angle $\phi$ between a line connecting a reference position of the second camera and the pupil center and the line-of-sight of the subject and calculating a formula $\theta=f(r^*)$ showing a relationship between $r^*$ related to r and $\theta$;

obtaining data on a coordinate point O' of the pupil position of the subject with the first camera by making the subject gaze at an unknown point G' in the coordinate system;

obtaining data of the corneal reflection center, a size of vector r' from the reflection center to the pupil center P, and an inclination $\phi'$ of the vector r' relative to the coordinate axis with the second camera; and calculating $\theta=f(r^{*\prime})$ from $r^{*\prime}$ related to r' by using the relational formula to further obtain the unknown point G' from $\phi'$ and $\theta'$.

8. A three-dimensional view-point measurement device, comprising: two cameras, a first light source arranged near one of the two cameras, a second light source arranged near another of the two cameras, a control means for controlling ON/OFF of the first light source and the second light source and obtaining an image signal in sync with ON/OFF, and a calculation means for extracting a pupil and corneal reflection from the obtained image signal.

9. The three-dimensional view-point measurement device according to claim 8, wherein the first light source and the second light source are configured to have an approximately identical emission wavelength.

10. A three-dimensional view-point measurement device, comprising: two cameras, a first light source arranged near one of the two cameras, a second light source arranged near another of the two cameras, a control means for controlling ON/OFF of the first light source and the second light source and obtaining an image signal in sync with ON/OFF, and a calculation means for extracting a pupil and corneal reflection from the obtained image signal and calculating a line of-sight vector from these positions.

11. The three-dimensional view-point measurement device according to claim 10, wherein the first light source and the second light source are configured to have an approximately identical emission wavelength.

12. A three-dimensional view-point measurement device, comprising: two cameras, a first light source arranged near one of the two cameras, a second light source arranged near another of the two cameras, a control means for controlling ON/OFF of the first light source and the second light source and obtaining an image signal in sync with ON/OFF, and a calculation means for extracting a pupil and corneal reflection from the obtained image signal and calculating a three-dimensional position of the pupil from these positions.

13. The three-dimensional view-point measurement device according to claim 12, wherein the first light source and the second light source are configured to have an approximately identical emission wavelength.

* * * * *